(12) United States Patent
Crowley et al.

(10) Patent No.: US 9,090,882 B2
(45) Date of Patent: Jul. 28, 2015

(54) COMPOSITIONS AND METHODS FOR ENHANCED AMINO ACID LEVELS IN PLANTS CONFERRED BY LYSINE AND/OR THREONINE FEEDBACK INSENSITIVE ASPARTATE KINASE PROTEINS

(75) Inventors: James H. Crowley, Manchester, MO (US); Barry S. Goldman, St. Louis, MO (US); Jintai Huang, Chesterfield, MO (US); Qungang Qi, Chesterfield, MO (US); William D. Rapp, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 719 days.

(21) Appl. No.: 12/997,860

(22) PCT Filed: Jun. 30, 2009

(86) PCT No.: PCT/US2009/049233
§ 371 (c)(1),
(2), (4) Date: Apr. 18, 2011

(87) PCT Pub. No.: WO2010/002876
PCT Pub. Date: Jan. 7, 2010

(65) Prior Publication Data
US 2011/0191898 A1 Aug. 4, 2011

Related U.S. Application Data

(60) Provisional application No. 61/077,043, filed on Jun. 30, 2008.

(51) Int. Cl.
*C12N 9/12* (2006.01)
*C12N 15/82* (2006.01)

(52) U.S. Cl.
CPC .......... *C12N 9/1217* (2013.01); *C12N 15/8251* (2013.01); *C12N 15/8254* (2013.01)

(58) Field of Classification Search
USPC ....................................................... 800/278
See application file for complete search history.

(56) References Cited

U.S. PATENT DOCUMENTS

| | | | |
|---|---|---|---|
| 5,661,012 A | 8/1997 | Sano et al. | |
| 7,071,383 B2 * | 7/2006 | Falco | 800/298 |
| 7,314,974 B2 | 1/2008 | Cao et al. | |
| 2003/0233675 A1 * | 12/2003 | Cao et al. | 800/279 |

FOREIGN PATENT DOCUMENTS

| | | |
|---|---|---|
| CN | 1107179 | 8/1995 |
| CN | 1242050 A | 1/2000 |
| EP | 0 485 970 A2 | 5/1992 |
| WO | WO 93/19190 A1 | 9/1993 |
| WO | WO 95/15392 A1 | 6/1995 |
| WO | WO 9515392 A1 * | 6/1995 |
| WO | WO98/22600 | 5/1998 |
| WO | WO 02/094867 A2 | 11/2002 |

OTHER PUBLICATIONS

Kobashi et al. (Kinetic and Mutation Analysis of Aspartate Kinase from Thermus flavus, 87 Journal of Bioscience and Bioengineering No. 6, 739-745 (1999)).*
Kikuchi et al. (Mutational analysis of the feedback sites of lysine-sensitive aspartokinase of *Escherichia coli*, 173 FEMS Microbiology Letters, 211-215 at 213-214 (1999)).*
Kotaka et al. (Structures of R- and T-state *Escherichia coli* Aspartokinase III: mechanisms of the allosteric transition and inhibition by lysine, 281 JBC No. 42, 31544-31552 at 31548-49 (2006)).*
Dotson et al. (Lysine-insensitive aspartate kinase in two threonine-overproducing mutants of maize, 182 Planta, 546-552 (1990)).*
Bareich et al. (Functionally important amino acids in *Saccharomyces cerevisiae* aspartate kinase, 311 Bioch and Biophys Res Comm, 597-603 (2003)).*
BLAST of SEQ ID No. 7 obtained Dec. 11, 2014.*
Karchi et al., "Seed specific expression of a bacterial desensitized aspartate kinase increases the production of seed threonine and methionine in transgenic tobacco," *Plant J.*, 3:721-727, 1993.
Rigden et al., "Plant virus DNA replication processes in agrobacterium: insight into the origins of geminiviruses," *Proc. Natl. Acad. Sci. USA*, 93:10280-10284, 1996.
English translation of office action issued Apr. 23, 2012, in Chinese Application No. 200980125099.5.

* cited by examiner

*Primary Examiner* — Cynthia Collins
*Assistant Examiner* — Rebecca Stephens
(74) *Attorney, Agent, or Firm* — Dentons US LLP; Chunping Li, Esq.

(57) ABSTRACT

Threonine is an essential amino acid for humans and in the animal feed industry where its levels in feed rations can significantly impact the cost of production of important meat sources, such as swine and poultry. Threonine as well as essential amino acids lysine and methionine are all synthesized via the aspartate family pathway. Aspartate kinase (AK) is the first enzyme in the pathway, and catalyzes the ATP-dependent phosphorylation of aspartate to form β-aspartyl phosphate. AK constitutes the main regulatory step controlling the metabolic flux through the pathway, and is subject to end product inhibition by Lys and/or Thr. The current invention provides a method to produce a transgenic high free threonine soybean via the overexpression of feedback-resistant AK enzymes in developing soybean plants and seeds. These modifications provide a method to enhance both plant nitrogen metabolism and crop growth performance.

32 Claims, 12 Drawing Sheets

Truncation analysis of *Xenorhabdus bovienii* AK

AK activity (µmoles·min$^{-1}$·mg$^{-1}$)

wt — 0.36 ± 0.04 (sensitive to Lys inhibition)

ΔN$_{20}$ — 0.01 ± 0.002 (sensitive to Lys inhibition)

ΔC$_{211}$ — No activity (expressed well, stable)

ΔC$_{113}$ — 0.15 ± 0.05 (unstable, insensitive to Lys)

Deletion 345-361 — 0.22 ± 0.02 (stable, insensitive to Lys)

FIG. 2

COMPOSITIONS AND METHODS FOR ENHANCED AMINO ACID LEVELS IN PLANTS CONFERRED BY LYSINE AND/OR THREONINE FEEDBACK INSENSITIVE ASPARTATE KINASE PROTEINS

REFERENCE TO RELATED APPLICATIONS

This application claims priority to U.S. Provisional Application No. 61/077,043, filed on Jun. 30, 2008.

INCORPORATION OF SEQUENCE LISTING

A sequence listing containing the file named MONS211WOsequencelisting.txt, which is 35 KB (as measured in Microsoft Windows®) and created on Jun. 9, 2009, comprises 23 nucleotide sequences, and is herein incorporated by reference in its entirety.

FIELD OF THE INVENTION

The present invention relates to the field of plant molecular biology and plant genetic engineering and polynucleotide molecules useful for gene expression in plants. Specifically, the present invention relates to genetic modifications to gene sequences that are useful in producing enhanced levels of amino acids in plants, for food and/or feed applications. The invention further discloses methods of producing and using said deregulated genes.

BACKGROUND

Monogastric animals, including humans, cannot synthesize the essential amino acids (EAAs) which include: lysine (Lys), methionine (Met) and threonine (Thr). Plants are the primary source of proteins and essential amino acids consumed by humans and livestock. However, the amino acid composition of plant seeds is not optimally balanced for human and livestock nutrition. Therefore, in the livestock industry, costly synthetic or microbe-synthesized EAAs are routinely purchased and used as supplements to grain-based and plant-based diets for animals in order to increase their growth and the nutritional value of livestock-derived products. Similarly, human food is often fortified with EAA supplements to promote growth or enhance health. This supplementation of food and feed results in substantially increased costs associated with these diets.

In organisms capable of synthesizing appropriate levels of threonine, as well as the essential amino acids lysine (Lys) and methionine (Met), are synthesized via the aspartate family pathway (FIG. 1). Aspartate kinase (AK), the first enzyme in the pathway, catalyzes the ATP-dependent phosphorylation of aspartate (Asp) to form β-aspartyl phosphate. AK constitutes the main regulatory step controlling the metabolic flux through the biosynthetic pathway and is subject to end-product inhibition by Lys and/or Thr. This end-product inhibition of biosynthetic enzymes such as AK results in limited levels of free essential amino acids in plant cells and necessitates supplementation with synthetic essential amino acids during the development of livestock animals and in human diets. A need therefore exists for strategies to increase the content of EAAs in plants and seeds such that they will be available for livestock and human diets.

The current invention provides an alternative approach to post-harvest food and feed supplementation by genetic modification of different crops.

SUMMARY

The present invention provides an isolated polynucleotide comprising a nucleic acid sequence encoding a polypeptide selected from the group consisting of SEQ ID NO: 7 through SEQ ID NO: 10.

In certain aspects, there is provided a polynucleotide sequence encoding a polypeptide at least 75%, 80%, 85%, 90%, 95%, 96%, 97%, 98%, 99% or 99.5% identical to the polypeptide sequence of SEQ ID NO: 7, SEQ ID NO: 8, SEQ ID NO: 9 or SEQ ID NO: 10, wherein polypeptide exhibits aspartate kinase (AK) activity that is not subject to end-product inhibition by lysine and/or threonine. A polynucleotide can, in some cases, encode a polypeptide having one or more amino acid substitutions, insertions or deletions relative to the wild type (wt) *Xenorhabdus bovienii* AK (i.e., encoded by SEQ ID NO: 6). For example, an encoded polypeptide may comprise a substitution at an amino acid position corresponding to position 257 and/or 359 in *X. bovienii* AK. In a further example, an encoded polypeptide may comprise a deletion of amino acids corresponding to positions 345-361 of wt *X. bovienii* AK.

In one embodiment, the present invention provides an isolated polynucleotide comprising a nucleic acid sequence selected from the group consisting of SEQ ID NO: 1 through SEQ ID NO: 5 or complements thereof.

In a further embodiment, there is provided a polynucleotide comprising a nucleic acid sequence at least 75%, 80%, 85%, 90%, 95%, 96%, 97%, 98%, 99% or 99.5% identical to the nucleic acid sequence of SEQ ID NO: 1, SEQ ID NO: 2, SEQ ID NO: 3, SEQ ID NO: 4, SEQ ID NO: 5 or SEQ ID NO: 6, wherein the nucleic acid sequence encodes a polypeptide that exhibits aspartate kinase (AK) activity that is not subject to end-product inhibition by lysine and/or threonine.

In another embodiment, there is provided a polynucleotide comprising a nucleic acid sequence that hybridizes under high stringency conditions to a full compliment of SEQ ID NO: 1, SEQ ID NO: 2, SEQ ID NO: 3, SEQ ID NO: 4, SEQ ID NO: 5 or SEQ ID NO: 6, wherein the nucleic acid sequence encodes a polypeptide that exhibits aspartate kinase (AK) activity that is not subject to end-product inhibition by lysine and/or threonine.

In another embodiment, the present invention provides an isolated polypeptide encoded by a polynucleotide of SEQ ID NO: 1 through SEQ ID NO: 5.

In another embodiment, the present invention provides an isolated polypeptide encoded by a polynucleotide disclosed herein. For example, the isolated polypeptide is, in some aspects, encoded by a polynucleotide selected from the group consisting of SEQ ID NO: 1 through SEQ ID NO: 5 wherein the polypeptide is selected from the group consisting of SEQ ID NO: 7 through SEQ ID NO: 10.

In another embodiment, the present invention provides a recombinant DNA construct comprising a polynucleotide disclosed herein, such as a polynucleotide comprising a nucleic acid sequence encoding a polypeptide selected from the group consisting of SEQ ID NO: 7 through SEQ ID NO: 10.

In another embodiment, the present invention provides a recombinant DNA construct comprising a polynucleotide disclosed herein, such as a polynucleotide comprising a nucleic acid sequence encoding a polypeptide selected from the group consisting of SEQ ID NO: 7 through SEQ ID NO: 10, wherein said polynucleotide is operably linked to a promoter functional in a plant cell.

It is an additional object of this invention to provide transformed cell or organism comprising a polynucleotide disclosed herein, such as a polynucleotide comprising a nucleic acid sequence encoding a polypeptide selected from the group consisting of SEQ ID NO: 7 through SEQ ID NO: 10; and a transformed cell or organism comprising said polynucleotide, wherein the organism is a plant selected from the group consisting of cotton, wheat, sugarcane, sugarbeets, soybean, rice, canola, corn, sorghum, barley, Brassica and Arabidopsis. In another embodiment, the present invention provides a method of producing a plant having an improved property as an animal feed or human food, wherein said method comprises transforming a plant with a recombinant construct comprising a promoter region functional in a plant cell operably joined to a polynucleotide comprising coding sequence for a polypeptide associated with said property, and growing said transformed plant, wherein said polypeptide is selected from the group consisting of SEQ ID NO: 7 through SEQ ID NO: 10. Said polypeptide may be modified to enhance threonine production, wherein said polypeptide comprises a sequence selected from the group consisting of SEQ ID NO: 7 through SEQ ID NO: 10. Said polypeptide may be useful for improving germination, wherein said polypeptide comprises a sequence selected from the group consisting of SEQ ID NO: 7 through SEQ ID NO: 10. Said polypeptide may also be useful for providing increased biomass or enhanced plant growth to a plant, wherein said polypeptide comprises a sequence selected from the group consisting of SEQ ID NO: 7 through SEQ ID NO: 10. Additionally, said polypeptide may be useful for improving crop productivity or grain composition by manipulating plant growth rate, wherein said polypeptide comprises a sequence selected from the group consisting of SEQ ID NO: 7 through SEQ ID NO: 10. Said modified polypeptide may also be useful for increasing the free amino acid level content of a seed by manipulating a polypeptide sequence, wherein said polypeptide comprises a sequence selected from the group consisting of SEQ ID NO: 7 through SEQ ID NO: 10. Said polypeptide may be useful for enhancing seed germination and growth by modification of the enzyme aspartate kinase, wherein said polypeptide comprises a sequence selected from the group consisting of SEQ ID NO: 7 through SEQ ID NO: 10. And said polypeptide may be useful for increased shoot biomass by modification of the aspartate family pathway, wherein said modification comprises the modification of the aspartate kinase polypeptide such that the modified sequence is selected from the group consisting of SEQ ID NO: 7 through SEQ ID NO: 10.

In yet a further embodiment, there is provided a plant part comprising a polynucleotide disclosed herein. For example, the plant part may be a plant leaf, a shoot, a root, a fruit or a seed. In still a further aspects, there is provided a product made from a plant part comprising a nucleic acid sequence disclosed herein. For example, a flour or meal comprising a polynucleotide according to the disclosure is provided. Plant products described herein may be further defined as a food products such as a human food or animal feed.

In another embodiment, the present invention provides a recombinant nucleic acid encoding an isolated polypeptide disclosed herein, such as a polypeptide of SEQ ID NO: 7 through SEQ ID NO: 10.

The present invention therefore provides a transgenic plant with a modified AK polypeptide comprising an AK amino acid sequence comprising at least one modification relative to a wild-type plant AK polypeptide, wherein said modified polypeptide comprises: a) an enzyme that catalyzes the ATP-dependent phosphorylation of aspartate to form beta-aspartyl phosphate; and b) wherein said modified AK polypeptide is not subject to end product inhibition by lysine and/or threonine. Said transgenic plant with a modified AK polypeptide may be selected from the group consisting of: Brassica napus, Arabidopsis thaliana, Glycine max, Zea mays, wheat, rice, alfalfa, sorghum, barley or cotton.

In another embodiment, the present invention provides a transgenic plant with a modified AK polypeptide comprising an AK amino acid sequence comprising at least one modification relative to a wild-type plant AK polypeptide, wherein said modified polypeptide comprises: a) an enzyme that catalyzes the ATP-dependent phosphorylation of aspartate to form beta-aspartyl phosphate; and b) wherein said modified AK polypeptide is not subject to end product inhibition by lysine and/or threonine wherein said at least one modification may comprise an amino acid substitution. The amino acid modification describe above may be a substitution to a non-alanine to alanine or a non-conservative substitution. Said amino acid substitution may be at a position selected from the group consisting of: a) a position corresponding to amino acid 257; and b) a position corresponding to amino acid 359. Said transgenic plant with a modified AK polypeptide may comprise at least one amino acid substitution. Alternatively, said transgenic plant with a modified AK polypeptide may comprise at least two amino acid substitutions, each amino acid substitution being at a position independently selected from the group consisting of: a) a position corresponding to amino acid 257; and b) a position corresponding to amino acid 359. Said transgenic plant AK polypeptide may be derived from Xenorhabdus bovienii; and one or more of the amino acid substitutions may be non-conservative substitutions(s) or they may be non-alanine to alanine substitutions(s). In said transgenic AK polypeptide, said at least one modification may comprise the truncation of the regulatory domain.

In another embodiment, said transgenic AK polypeptide comprises SEQ ID NO: 8.

In another embodiment, said transgenic AK polypeptide will not bind lysine.

The present invention therefore provides seed comprising a modified AK polypeptide, that when grown provides an enhanced level of threonine as compared to the non-transgenic line from which the modified plant is derived.

In a further embodiment, the present invention provides a recombinant nucleic acid encoding a polypeptide, disclosed herein, such as a polypeptide selected from the group consisting of SEQ ID NO: 7 through SEQ ID NO: 10, which is an expression vector further comprising a promoter region operably linked to the recombinant nucleic acid. Additionally, the present invention provides a vector comprising a replicon and the recombinant nucleic acid encoding a polypeptide selected from the group consisting of SEQ ID NO: 7 through SEQ ID NO: 10. Said expression vector comprises a promoter region, wherein the promoter region is operable in a plant cell. Said promoter region may comprise a CaMV 35S promoter, a 7s-alpha' (7Sα') promoter or a USP99 promoter. Said promoter region is transcriptionally active in a tissue- and/or organ-specific fashion.

In another embodiment, the present invention provides a transgenic plant comprising a transgene encoding a transgenic AK polypeptide, said transgenic plant expressing a higher levels of the amino acid threonine in its tissues. Said transgenic plant may also express higher levels of other amino acids such as arginine, asparagine, glutamine, serine methionine and lysine. Said transgenic plant may be a monocotyledonous plant or a dicotyledonous plant.

In another embodiment, the present invention provides transgenic plant comprising a transgene encoding a transgenic AK polypeptide, said transgenic plant expressing a higher levels of an amino acid in its tissues, wherein said AK polypeptide is an enzyme in the aspartate family pathway.

In another embodiment, the present invention provides a transgenic plant comprising a transgene encoding a transgenic AK polypeptide, said transgenic plant expressing a higher levels of the amino acid threonine in its tissues where the plant or a portion thereof is used as feed.

In another embodiment, the present invention provides a transgenic plant comprising a transgene encoding a transgenic AK polypeptide, said transgenic plant expressing a higher levels of the amino acid threonine in its tissues where the plant or a portion thereof is used as human food.

In another embodiment, the present invention provides a transgenic plant comprising a transgene encoding a transgenic AK polypeptide, said transgenic plant expressing a higher levels of the amino acid threonine in its tissues wherein the amino acid substitution in the transgenic AK polypeptide is a non-alanine to alanine substitution or a substitution of an amino acid with an oppositely charged amino acid.

In another embodiment, the present invention provides a transgenic plant comprising a transgene encoding a transgenic AK polypeptide, said transgenic plant expressing a higher levels of the amino acid threonine in its tissues wherein at least one modification in the transgenic AK polypeptide is within the EAAEMA motif or the ALTLDTTG motif.

In another embodiment, the present invention provides a transgenic plant comprising a transgene encoding a transgenic AK polypeptide, said transgenic plant expressing a higher levels of the amino acid threonine in its tissues wherein at least one of the amino acid substitutions in said transgenic AK polypeptide is a non-alanine to alanine substitution or a substitution of an amino acid with an oppositely charged amino acid.

In another embodiment, the present invention provides a transgenic plant with a modified AK polypeptide comprising an AK amino acid sequence comprising at least one modification relative to a wild-type plant AK polypeptide, wherein said modified polypeptide comprises: a) an enzyme that catalyzes the ATP-dependent phosphorylation of aspartate to form beta-aspartyl phosphate; and b) wherein said modified AK polypeptide is not subject to end product inhibition by lysine and/or threonine wherein said at least one modification may comprise an amino acid substitution; and wherein each of the amino acid substitutions is a non-alanine to alanine substitution or a substitution of an amino acid with an oppositely charged amino acid.

In another embodiment, the present invention provides a transgenic plant with a modified AK polypeptide comprising an AK amino acid sequence comprising at least one modification relative to a wild-type plant AK polypeptide, wherein said modified polypeptide comprises: a) an enzyme that catalyzes the ATP-dependent phosphorylation of aspartate to form beta-aspartyl phosphate; and b) wherein said modified AK polypeptide is not subject to end product inhibition by lysine and/or threonine wherein said at least one modification may comprise an amino acid substitution, said amino acid substitution being at a position independently selected from the group consisting of: (a) a position corresponding to amino acid 257; and (b) a position corresponding to amino acid 359, wherein the amino acid substitution at the position corresponding to amino acid 257 is a non-alanine to alanine substitution or a non-conservative substitution.

In another embodiment, the present invention provides a transgenic plant with a modified AK polypeptide comprising an AK amino acid sequence comprising at least one modification relative to a wild-type plant AK polypeptide, wherein said modified polypeptide comprises: a) an enzyme that catalyzes the ATP-dependent phosphorylation of aspartate to form beta-aspartyl phosphate; and b) wherein said modified AK polypeptide is not subject to end product inhibition by lysine and/or threonine wherein said at least one modification may comprise an amino acid substitution, said amino acid substitution being at a position independently selected from the group consisting of: (a) a position corresponding to amino acid 257; and (b) a position corresponding to amino acid 359, wherein the amino acid substitution at the position corresponding to amino acid 359 is a non-alanine to alanine substitution or a non-conservative substitution.

In another embodiment, the present invention provides a method of producing a transgenic plant comprising a transgene encoding a transgenic AK polypeptide, said transgenic plant expressing a higher levels of the amino acid threonine in its tissues, said method comprising introducing into a plant a vector comprising the transgene encoding the transgenic AK polypeptide.

In another embodiment, there is provided a method for producing a transformed plant comprising, obtaining a plant cell comprising a polynucleotide sequence of the instant disclosure and regenerating a plant from the polynucleotide sequence.

In another embodiment, the present invention provides a method for producing a modified plant line having an increased amount of at least one amino acid as compared to an unmodified parent plant line comprising the steps of introducing into a plant a genetic alteration of a DNA sequence for an aspartate kinase enzyme.

In another embodiment, the present invention provides a method for producing a modified plant line having an increased amount of threonine as compared to an unmodified parent plant line comprising the steps of introducing into a plant a genetic alteration of a DNA sequence for an aspartate kinase enzyme.

In another embodiment, the present invention provides a method for producing a modified plant line having an increased amount of threonine as compared to an unmodified parent plant line, wherein the modified plant line comprises a 2- to 100-fold increase in threonine levels in plant tissue, comprising the steps of introducing into a plant a genetic alteration of a DNA sequence for an aspartate kinase enzyme.

In another embodiment, the present invention provides a method for producing a modified plant line having an increased amount of threonine as compared to an unmodified parent plant line, wherein the modified plant line comprises a 5- to 100-fold increase in threonine levels in plant tissue, comprising the steps of introducing into a plant a genetic alteration of a DNA sequence for an aspartate kinase enzyme.

In another embodiment, the present invention provides a method for producing a modified plant line having an increased amount of threonine as compared to an unmodified parent plant line, wherein the modified plant line comprises a 100-fold increase in threonine levels in plant tissue, comprising the steps of introducing into a plant a genetic alteration of a DNA sequence for an aspartate kinase enzyme.

In another embodiment, the present invention provides a method for increasing the total free amino acid content of a plant or transformed progeny thereof, comprising; transforming a plant with a plant transformation vector comprising an isolated polynucleotide encoding a modified aspartate kinase, that increases the free amino acid content of the transformed plant compared to an untransformed control.

In another embodiment, the present invention provides a method for increasing the total free amino acid content of a plant or transformed progeny thereof, comprising; transforming a plant with a plant transformation vector comprising an isolated polynucleotide encoding a modified aspartate kinase, that increases the free amino acid content of the transformed plant compared to an untransformed control, wherein the vector comprises the nucleotide sequence of SEQ ID NO: 1.

In another embodiment, the present invention provides a method for increasing the total free amino acid content of a plant or transformed progeny thereof, comprising; transforming a plant with a plant transformation vector comprising an isolated polynucleotide encoding a modified aspartate kinase, that increases the free amino acid content of the transformed plant compared to an untransformed control, wherein the vector comprises the nucleotide sequence of SEQ ID NO: 2.

In another embodiment, the present invention provides a method for increasing the total free amino acid content of a plant or transformed progeny thereof, comprising; transforming a plant with a plant transformation vector comprising an isolated polynucleotide encoding a modified aspartate kinase, that increases the free amino acid content of the transformed plant compared to an untransformed control, wherein the vector comprises the nucleotide sequence of SEQ ID NO: 3.

In another embodiment, the present invention provides a method for increasing the total free amino acid content of a plant or transformed progeny thereof, comprising; transforming a plant with a plant transformation vector comprising an isolated polynucleotide encoding a modified aspartate kinase, that increases the free amino acid content of the transformed plant compared to an untransformed control, wherein the vector comprises the nucleotide sequence of SEQ ID NO: 4.

In another embodiment, the present invention provides a method for increasing the total free amino acid content of a plant or transformed progeny thereof, comprising; transforming a plant with a plant transformation vector comprising an isolated polynucleotide encoding a modified aspartate kinase, that increases the free amino acid content of the transformed plant compared to an untransformed control wherein the transformed plant or progeny thereof is selected from the group consisting of soybean, canola, corn, sorghum or cotton.

In another embodiment, the present invention provides a method for increasing the total free amino acid content of a plant or transformed progeny thereof, comprising; transforming a plant with a plant transformation vector comprising an isolated polynucleotide encoding a modified aspartate kinase, that increases the free amino acid content of the transformed plant compared to an untransformed control wherein the amino acids are one or more essential amino acids.

In another embodiment, the present invention provides a method for increasing the total free amino acid content of a plant or transformed progeny thereof, comprising; transforming a plant with a plant transformation vector comprising an isolated polynucleotide encoding a modified aspartate kinase, that increases the free amino acid content of the transformed plant compared to an untransformed control wherein the vector further comprises one or more operably linked regulatory nucleotide sequences.

In another embodiment, the present invention provides a method for increasing the total free amino acid content of a plant or transformed progeny thereof, comprising; transforming a plant with a plant transformation vector comprising an isolated polynucleotide encoding a modified aspartate kinase, that increases the free amino acid content of the transformed plant compared to an untransformed control wherein the vector further comprises one or more operably linked regulatory nucleotide sequences, wherein the one or more regulatory nucleotide sequences are selected from the group consisting of promoters, terminators, translation enhancers, nucleotide sequences for replication in a suitable host cell, nucleotide sequences for integration into a genome, and combinations thereof.

In another embodiment, the present invention provides a method for increasing the total free amino acid content of a plant or transformed progeny thereof, comprising; transforming a plant with a plant transformation vector comprising an isolated polynucleotide encoding a modified aspartate kinase, that increases the free amino acid content of the transformed plant compared to an untransformed control wherein the transformed plant, progeny thereof, the seed thereof, or the oil thereof is used indirectly as food or feed.

In another embodiment, the present invention provides a transgenic plant having a gene construct comprising a modified aspartate kinase that will enhance nitrogen assimilation/metabolism enzyme such that the nitrogen assimilation/metabolism enzyme is overexpressed in the transgenic plant, and the transgenic plant exhibits: i) faster rate of growth, ii) greater fresh or dry weight at maturation, iii) greater fruit or seed yield, iv) greater total plant nitrogen content, v) greater fruit or seed nitrogen content, vi) greater free amino acid content in the whole plant, vii) greater free amino acid content in the fruit or seed, viii) greater protein content in seed or fruit, or ix) greater protein content in a vegetative tissue, than a progenitor plant which does not contain the gene construct.

In another embodiment, the present invention provides a transgenic plant having a gene construct comprising a modified aspartate kinase that will enhance nitrogen assimilation/metabolism enzyme such that the nitrogen assimilation/metabolism enzyme is overexpressed in the transgenic plant, and the transgenic plant exhibits: i) faster rate of growth, ii) greater fresh or dry weight at maturation, iii) greater fruit or seed yield, iv) greater total plant nitrogen content, v) greater fruit or seed nitrogen content, vi) greater free amino acid content in the whole plant, vii) greater free amino acid content in the fruit or seed, viii) greater protein content in seed or fruit, or ix) greater protein content in a vegetative tissue, than a progenitor plant which does not contain the gene construct, further comprising a plant promoter.

In another embodiment, the present invention provides a transgenic plant having a gene construct comprising a modified aspartate kinase that will enhance nitrogen assimilation/metabolism enzyme such that the nitrogen assimilation/metabolism enzyme is overexpressed in the transgenic plant, and the transgenic plant exhibits: i) faster rate of growth, ii) greater fresh or dry weight at maturation, iii) greater fruit or seed yield, iv) greater total plant nitrogen content, v) greater fruit or seed nitrogen content, vi) greater free amino acid content in the whole plant, vii) greater free amino acid content in the fruit or seed, viii) greater protein content in seed or fruit, or ix) greater protein content in a vegetative tissue, than a progenitor plant which does not contain the gene construct, further comprising a plant promoter, wherein the plant promoter is CaMV 35S promoter.

In another embodiment, the present invention provides a transgenic plant having a gene construct comprising a modified aspartate kinase that will enhance nitrogen assimilation/metabolism enzyme such that the nitrogen assimilation/metabolism enzyme is overexpressed in the transgenic plant, and the transgenic plant exhibits: i) faster rate of growth, ii) greater fresh or dry weight at maturation, iii) greater fruit or seed yield, iv) greater total plant nitrogen content, v) greater fruit or seed nitrogen content, vi) greater free amino acid content in the whole plant, vii) greater free amino acid content in the fruit or seed, viii) greater protein content in seed or fruit, or ix) greater protein content in a vegetative tissue, than a progenitor plant which does not contain the gene construct, further comprising a plant promoter, wherein the plant promoter is the USP99 promoter.

In another embodiment, the present invention provides a transgenic plant having a gene construct comprising a modified aspartate kinase that will enhance nitrogen assimilation/metabolism enzyme such that the nitrogen assimilation/metabolism enzyme is overexpressed in the transgenic plant, and the transgenic plant exhibits: i) faster rate of growth, ii) greater fresh or dry weight at maturation, iii) greater fruit or seed yield, iv) greater total plant nitrogen content, v) greater fruit or seed nitrogen content, vi) greater free amino acid content in the whole plant, vii) greater free amino acid content in the fruit or seed, viii) greater protein content in seed or fruit, or ix) greater protein content in a vegetative tissue, than a progenitor plant which does not contain the gene construct, further comprising a plant promoter, wherein the plant promoter is 7Sα' promoter.

In another embodiment, the present invention provides a seed from a transgenic plant having a gene construct comprising a modified aspartate kinase that will enhance nitrogen assimilation/metabolism enzyme such that the nitrogen assimilation/metabolism enzyme is overexpressed in the transgenic plant, and the transgenic plant exhibits: i) faster rate of growth, ii) greater fresh or dry weight at maturation, iii) greater fruit or seed yield, iv) greater total plant nitrogen content, v) greater fruit or seed nitrogen content, vi) greater free amino acid content in the whole plant, vii) greater free amino acid content in the fruit or seed, viii) greater protein content in seed or fruit, or ix) greater protein content in a vegetative tissue, than a progenitor plant which does not contain the gene construct, further comprising a plant promoter, wherein the seed contains the transgenic gene construct.

In another embodiment, the present invention provides a progeny, clone, cell line or cell of a transgenic plant having a gene construct comprising a modified aspartate kinase that will enhance nitrogen assimilation/metabolism enzyme such that the nitrogen assimilation/metabolism enzyme is overexpressed in the transgenic plant, and the transgenic plant exhibits: i) faster rate of growth, ii) greater fresh or dry weight at maturation, iii) greater fruit or seed yield, iv) greater total plant nitrogen content, v) greater fruit or seed nitrogen content, vi) greater free amino acid content in the whole plant, vii) greater free amino acid content in the fruit or seed, viii) greater protein content in seed or fruit, or ix) greater protein content in a vegetative tissue, than a progenitor plant which does not contain the gene construct, further comprising a plant promoter, wherein said progeny, clone, cell line or cell has the transgenic gene construct.

In another embodiment, the present invention provides a transgenic plant or a progenitor plant thereof having a gene construct comprising a modified aspartate kinase that will enhance nitrogen assimilation/metabolism enzyme such that the nitrogen assimilation/metabolism enzyme is overexpressed in the transgenic plant, and the transgenic plant exhibits: i) faster rate of growth, ii) greater fresh or dry weight at maturation, iii) greater fruit or seed yield, iv) greater total plant nitrogen content, v) greater fruit or seed nitrogen content, vi) greater free amino acid content in the whole plant, vii) greater free amino acid content in the fruit or seed, viii) greater protein content in seed or fruit, or ix) greater protein content in a vegetative tissue, than a progenitor plant which does not contain the gene construct, further comprising a plant promoter, wherein the transgenic and progenitor plants thereof are selected from the group consisting of Arabidopsis, maize, wheat, rice, soybean, or Brassica.

In another embodiment, the present invention provides a method of producing a transgenic plant having an improved agronomic or nutritional characteristic, which method comprises identifying a transgenic plant overexpressing a modified aspartate kinase from among transgenic plants not having a gene construct comprising a gene encoding a modified aspartate kinase.

In another embodiment, the present invention provides a method for producing a modified plant line having an increased amount of arginine as compared to an unmodified parent plant line comprising the steps of introducing into a plant a genetic alteration of a DNA sequence for an aspartate kinase enzyme.

In another embodiment, the present invention provides a method for producing a modified plant line having an increased amount of arginine as compared to an unmodified parent plant line, wherein the modified plant line comprises a 2-fold increase in arginine levels in plant tissue, comprising the steps of introducing into a plant a genetic alteration of a DNA sequence for an aspartate kinase enzyme.

In another embodiment, the present invention provides a method for producing a modified plant line having an increased amount of asparagine as compared to an unmodified parent plant line comprising the steps of introducing into a plant a genetic alteration of a DNA sequence for an aspartate kinase enzyme.

In another embodiment, the present invention provides a method for producing a modified plant line having an increased amount of asparagine as compared to an unmodified parent plant line, wherein the modified plant line comprises a 2- to 6-fold increase in asparagine levels in plant tissue, comprising the steps of introducing into a plant a genetic alteration of a DNA sequence for an aspartate kinase enzyme.

In another embodiment, the present invention provides a method for producing a modified plant line having an increased amount of glutamine as compared to an unmodified parent plant line comprising the steps of introducing into a plant a genetic alteration of a DNA sequence for an aspartate kinase enzyme.

In another embodiment, the present invention provides a method for producing a modified plant line having an increased amount of at glutamine as compared to an unmodified parent plant line, wherein the modified plant line comprises a 2-fold increase in glutamine levels in plant tissue, comprising the steps of introducing into a plant a genetic alteration of a DNA sequence for an aspartate kinase enzyme.

In another embodiment, the present invention provides a method for producing a modified plant line having an increased amount of serine as compared to an unmodified parent plant line comprising the steps of introducing into a plant a genetic alteration of a DNA sequence for an aspartate kinase enzyme.

In another embodiment, the present invention provides a method for producing a modified plant line having an increased amount of serine as compared to an unmodified parent plant line, wherein the modified plant line comprises a 10- to 30-fold increase in serine levels in plant tissue, comprising the steps of introducing into a plant a genetic alteration of a DNA sequence for an aspartate kinase enzyme.

In another embodiment, the present invention provides a method for producing a modified plant line having an increased amount of methionine as compared to an unmodified parent plant line comprising the steps of introducing into a plant a genetic alteration of a DNA sequence for an aspartate kinase enzyme.

In another embodiment, the present invention provides a method for producing a modified plant line having an increased amount of methionine as compared to an unmodified parent plant line, wherein the modified plant line comprises a 2- to 5-fold increase in methionine levels in plant tissue, comprising the steps of introducing into a plant a genetic alteration of a DNA sequence for an aspartate kinase enzyme.

In another embodiment, the present invention provides a method for producing a modified plant line having an increased amount of lysine as compared to an unmodified parent plant line comprising the steps of introducing into a plant a genetic alteration of a DNA sequence for an aspartate kinase enzyme.

In another embodiment, the present invention provides a method for producing a modified plant line having an increased amount of lysine as compared to an unmodified parent plant line, wherein the modified plant line comprises a 2-fold increase in lysine levels in plant tissue, comprising the steps of introducing into a plant a genetic alteration of a DNA sequence for an aspartate kinase enzyme.

Embodiments discussed in the context of a methods and/or composition of the invention may be employed with respect to any other method or composition described in this applications. Thus, an embodiment pertaining to one method or composition may be applied to other methods and compositions of the invention as well.

BRIEF DESCRIPTION OF THE DRAWINGS

FIG. 2: Truncation analysis of *Xenorhabdus bovienii* aspartate kinase (AK)

BRIEF DESCRIPTION OF THE SEQUENCES

Figure 1:
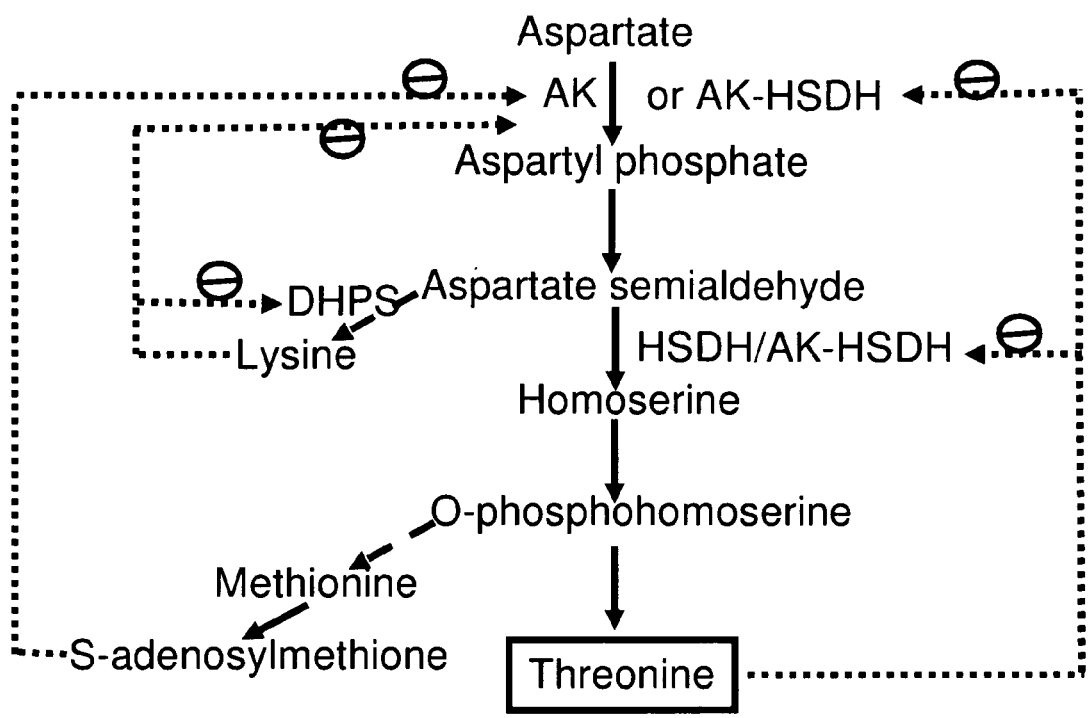
FIG. 1: Schematic Diagram of the Aspartate Family Biosynthetic Pathway

SEQ ID NO: 1 *X. bovienii*.AK.E257K DNA; corresponds to pMON101818
SEQ ID NO: 2 *X. bovienii*.AK.T359I DNA; corresponds to pMON101819 and pMON101820
SEQ ID NO: 3 *X. bovienii*.AK.T359I.nno DNA; corresponds to pMON101821 and pMON101822

SEQ ID NO: 4 *X. bovienii*.AK.E257K/T359I DNA

SEQ ID NO: 5 *X. bovienii*.AK-ΔN-345 to 361 DNA; corresponds to pMON81689

SEQ ID NO: 6 *X. bovienii*.AK.wild-type DNA; corresponds to pMON101817

SEQ ID NO: 7 *X. bovienii*.AK.E257K amino acid sequence

SEQ ID NO: 8 *X. bovienii*.AK.T359I amino acid sequence

SEQ ID NO: 9 *X. bovienii*.AK.E257K/T359I amino acid sequence

SEQ ID NO: 10 *X. bovienii*.AK-ΔN-345 to 361 amino acid sequence

SEQ ID NO: 11 Forward PCR primer for isolating Xb.AK from genomic DNA

SEQ ID NO: 12 Reverse PCR primer for isolating Xb.AK from genomic DNA

SEQ ID NO: 13 Chloroplast Targeting Peptide (CTP1)

SEQ ID NO: 14 Forward PCR primer for isolating *E. coli* lysC

SEQ ID NO: 15 Reverse PCR primer for isolating *E. coli* lysC

SEQ ID NO: 16 *E. coli* feedback-insensitive (T352I) lysC DNA

SEQ ID NO: 17 *E. coli* feedback-insensitive (T352I) lysC amino acid sequence

SEQ ID NO: 18 XbAKXhoIRv Reverse primer

SEQ ID NO: 19 XbAKNdeIFr Forward primer

SEQ ID NO: 20 XbAKE257KFr Forward primer

SEQ ID NO: 21 XbAKE257KRv Reverse primer

SEQ ID NO: 22 XbAKT359IFr Forward primer

SEQ ID NO: 23 XbAKT359IRv Reverse primer

DETAILED DESCRIPTION OF THE INVENTION

The present invention provides isolated DNAs, vectors, host cells and transgenic plants comprising an isolated nucleic acid encoding a modified aspartate kinase gene capable of providing high levels of threonine and other aspartate-derived amino acids upon expression within the plant. In one embodiment, the isolated nucleic acid encodes a modified aspartate kinase (AK). In other embodiments, the isolated nucleic acid encodes an aspartate kinase that is substantially resistant to inhibition by free lysine. Expression of the modified aspartate kinase elevates the level of threonine, e.g., free threonine in the seed, over the level present in the plant absent such expression.

Methods are also provided for producing transgenic plants having nucleic acids associated with increased aspartate kinase activity, and producing cultured cells, plant tissues, plants, plant parts and seeds that produce high levels of threonine. Such transgenic plants can preferably sexually transmit the ability to produce high levels of threonine to their progeny. Also described are methods for producing isolated DNAs encoding modified aspartate kinase, and cell culture selection techniques to select for novel genotypes that overproduce threonine and/or are resistant to feedback inhibition by lysine. For example, to produce soybean lines capable of producing high levels of threonine, transgenic soybean cells that contain at least one of the isolated DNAs of the present invention, are prepared and characterized, then regenerated into plants. Some of the isolated DNAs are resistant to growth inhibition by lysine. The methods provided in the present invention may also be used to produce increased levels of free threonine in dicot plants, such as other legumes, as well as in monocots, such as the cereal grains.

In the context of this disclosure, a number of terms shall be utilized. The terms "polynucleotide", "polynucleotide sequence", and "nucleic acid sequence" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 1300 contiguous nucleotides derived from SEQ ID NOs: 1, 2, 3, 4 or 5.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. Isolated polynucleotides may be purified from a host cell in which they naturally occur. Conventional nucleic acid purification methods known to those of skill in the art may be used to obtain isolated polynucleotides. The term also embraces recombinant polynucleotides and chemically synthesized polynucleotides.

As used herein, "altered" levels of threonine in a transformed plant, plant tissue, plant part or plant cell are levels which are greater or lesser than the levels found in the corresponding untransformed plant, plant tissue, plant part or plant cell.

The phrase "consists essentially of" as used with respect to the present DNA molecules, sequences or segments is defined to mean that a major portion of the DNA molecule, sequence or segment encodes an aspartate kinase. Unless otherwise indicated, the DNA molecule, sequence or segment generally does not encode proteins other than an aspartate kinase.

The term "complementary to" is used herein to mean that the sequence of a nucleic acid strand could hybridize to all, or a portion, of a reference polynucleotide sequence. For illustration, the nucleotide sequence "TATAC" has 100% identity to a reference sequence 5'-TATAC-3' but is 100% complementary to a reference sequence 5'-GTATA-3'.

As used herein, an "exogenous" aspartate kinase is an aspartate kinase that is encoded by an isolated DNA that has been introduced into a host cell, and that is preferably not identical to any DNA sequence present in the cell in its native, untransformed state. An "endogenous" or "native" aspartate kinase is an aspartate kinase that is naturally present in a host cell or organism.

As used herein, "increased," "high" or "elevated" levels of free threonine in a plant cell, plant tissue, plant part or plant are levels that are about 2 to 100 times, preferably about 5 to 100 times, and more preferably about 10-100 times, the levels found in an untransformed plant cell, plant tissue, plant part or plant, i.e., one where the genome has not been altered by the presence of an exogenous aspartate kinase nucleic acid or domain thereof. For example, the levels of free threonine in a transformed plant seed are compared with those in an untransformed plant seed ("the starting material").

DNA molecules encoding an aspartate kinase, and DNA molecules encoding a transit peptide or marker/reporter gene are "isolated" in that they were taken from their natural source and are no longer within the cell where they normally exist. Such isolated DNA molecules may have been at least partially prepared or manipulated in vitro, e.g., isolated from a cell in which they are normally found, purified, and amplified. Such isolated DNA molecules can also be "recombinant" in that they have been combined with exogenous DNA molecules or segments. For example, a recombinant DNA can be an isolated DNA that is operably linked to an exogenous promoter, or to a promoter that is endogenous to the host cell. The term embraces nucleic acids that are biochemically purified so as to substantially remove contaminating nucleic acids and other cellular components. The term also embraces recombinant nucleic acids and chemically synthesized nucleic acids.

As used herein, a "native" gene means a gene that has not been changed in vitro, i.e., a "wild-type" gene that has not been mutated in vitro.

The term "plastid" refers to the class of plant cell organelles that includes amyloplasts, chloroplasts, chromoplasts, elaioplasts, eoplasts, etioplasts, leucoplasts, and proplastids. These organelles are self-replicating, and contain what is commonly referred to as a "chloroplast genome," a circular DNA molecule that ranges in size from about 120 to about 217 kb, depending upon the plant species, and which usually contains an inverted repeat region.

As used herein, "polypeptide" means a continuous chain of amino acids that are all linked together by peptide bonds, except for the N-terminal and C-terminal amino acids that have amino and carboxylate groups, respectively, and that are not linked in peptide bonds. Polypeptides can have any length and can be post-translationally modified, for example, by glycosylation or phosphorylation.

The term "5' UTR" refers to the untranslated region of DNA upstream, or 5', of the coding region of a gene.

The term "3' UTR" refers to the untranslated region of DNA downstream, or 3', of the coding region of a gene.

The term "substantially homologous" refers to two sequences which are at least about 90% identical in sequence, as measured by the BestFit program described herein (Version 10; Genetics Computer Group, Inc., University of Wisconsin Biotechnology Center, Madison, Wis.), using default parameters.

The percent of sequence identity is preferably determined using the "Best Fit" or "Gap" program of the Sequence Analysis Software Package (Version 10; Genetics Computer Group, Inc., University of Wisconsin Biotechnology Center, Madison, Wis.). "Gap" utilizes the algorithm of Needleman and Wunsch (1970) to find the alignment of two sequences that maximizes the number of matches and minimizes the number of gaps.

"BestFit" performs an optimal alignment of the best segment of similarity between two sequences and inserts gaps to maximize the number of matches using the local homology algorithm of Smith and Waterman (Smith and Waterman, 1981; Smith et al., 1983). The percent identity is most preferably determined using the Best Fit program using default parameters. As used herein, the term "operatively linked" means that a promoter is connected to a coding region in such a way that the transcription of that coding region is controlled and regulated by that promoter. Means for operatively linking a promoter to a coding region are well known in the art.

The term "substantially identical" as used herein, refers to a comparison of polynucleotide molecules that encode the same or nearly the same protein or polypeptide. The four letter genetic code (A, G, C, and T/U) comprises three letter codons that direct t-RNA molecules to assemble amino acids into a polypeptide from an mRNA template. Having more than one codon that may code for the same amino acid is referred to as degenerate. Degenerate codons are used to construct substantially identical polynucleotide molecules that encode the same polypeptide where these polynucleotide molecules have a sequence of nucleotides when compared along their entire length in which they are at least 85% identical to one another, more preferably 86 to 90% identical to one another, even more preferably 91 to 95% identical to one another, or most preferably 96 to 99% identical to one another. Such sequences may differ due to changes at one or more bases, including a coding region with a truncation or deletion, yet still encode a polypeptide with aspartate kinase activity.

A "non-native polynucleotide" as used in the present invention is a DNA sequence designed according to the methods of the present invention and created as an isolated DNA molecule for use in a DNA construct that provides expression of a protein in host cells, and for the purposes of cloning into appropriate constructs or other uses known to those skilled in the art. Computer programs are available for these purposes, including but not limited to the "BestFit" or "Gap" programs of the Sequence Analysis Software Package, Genetics Computer Group (GCG), Inc., University of Wisconsin Biotechnology Center, Madison, Wis. 53711. The non-native polynucleotide may be created by one or more methods known in the art that include, but are not limited to, overlapping PCR and chemical synthesis. A non-native polynucleotide molecule of the present invention is substantially identical to other polynucleotides that code for the identical or nearly identical protein.

The term "translation" refers to the production the corresponding gene product, i.e., a peptide, polypeptide, or protein from an mRNA.

As used herein, the term "nutritionally enhanced" refers to an elevated, increased or high level of a particular amino acid in a plant cell as compared to the level of the same amino acid found in an untransformed plant cell, plant tissue, plant part or plant, i.e., one where the genome has not been altered by the presence of an exogenous nucleic acid. For example, the levels of free threonine in a transformed plant seed are compared with those in an untransformed plant seed ("the starting material").

As used herein, "expression" is the process of the transcription of a gene to produce the corresponding mRNA and translation of this mRNA to produce the corresponding gene product (i.e., a peptide, polypeptide, or protein).

"Enhanced expression" refers to an elevated, increased or high level of a particular amino acid in a plant cell as compared to the level of the same amino acid found in an untransformed plant cell, plant tissue, plant part or plant, i.e., one where the genome has not been altered by the presence of an exogenous nucleic acid.

As used herein, "feed" refers to materials available for feeding animals which includes without limitation forage, fodder and concentrates.

As used herein, "Food" refers to substances which are ingested by humans and contain nutrients which can be metabolized to produce energy.

The term "gene", as used herein, refers to chromosomal DNA, plasmid DNA, cDNA, synthetic DNA, or other DNA that encodes a peptide, polypeptide, protein, or RNA molecule.

A host or host organism includes bacteria cells, fungi, animals and animal cells, plants and plant cells, or any plant parts or tissues including protoplasts, calli, roots, tubers, seeds, stems, leaves, seedlings, embryos, and pollen.

Transformation, as used herein, refers to the introduction of nucleic acid into a recipient host. A cell that has undergone transformation as defined above is considered to be a transformed cell. An organism that has undergone transformation as defined above is considered to be a transformed organism.

Transgene, as used herein, is any piece of a nucleic acid molecule that is inserted by artifice into a cell, or an ancestor thereof, and becomes part of the genome of the plant or animal which develops from that cell. Such a transgene may include a gene which is partly or entirely exogenous (i.e., foreign) to the transgenic plant or animal, or may represent a gene having identity to an endogenous gene of the plant or animal.

The meaning of "transgenic", as used herein, is any cell that includes a nucleic acid molecule that has been inserted by artifice into a cell, or an ancestor thereof, and becomes part of the genome of the plant or animal which develops from that cell.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

The term "plasmid" refers to a circular double-stranded (ds) DNA construct that is used as a cloning vector, and that forms an extrachromosomal self-replicating genetic element in many bacteria and some eukaryotes.

Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. This is what is meant to be understood by the term "non-alanine to alanine substitution" or "non-conservative substitution".

Similarly, changes that result in substitution of one negatively charged residue for another, such as aspartic acid for glutamic acid, or one positively charged residue for another, such as lysine for arginine, can also be expected to produce a functionally equivalent product, and are referred to as "conservative substitutions". Nucleotide changes that result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

A variant or modified amino acid sequence is one in which a substitution, either non-alanine to alanine, non-conservative, or conservative, has altered one or more amino acids in the sequence. In making such changes, the hydropathic index of amino acids may be considered. The importance of the hydropathic amino acid index in conferring interactive biological function on a protein is generally understood in the art (Kyte and Doolittle, *J. Mol. Biol.*, 157: 105-132, 1982). It is accepted that the relative hydropathic character of the amino acid contributes to the secondary structure of the resultant protein, which in turn defines the interaction of the protein with other molecules, for example, substrates.

Each amino acid has been assigned a hydropathic index on the basis of their hydrophobicity and charge characteristics. These are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 (Hopp) states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine. Changes which are not expected to be advantageous may also be used if these resulted proteins having improved rumen resistance, increased resistance to proteolytic degradation, or both improved rumen resistance and increased resistance to proteolytic degradation, relative to the unmodified polypeptide from which they are engineered.

The term "hybridization" refers generally to the ability of nucleic acid molecules to join via complementary base strand pairing. Such hybridization may occur when nucleic acid molecules are contacted under appropriate conditions (see also, "high stringency conditions," below).

The term "high stringency conditions" in the context of hybridization is well known to the art, (see, e.g. sections 0.47-9.51 of Sambrook et al., (1989); and Sambrook and Russell, (2001), incorporated herein by reference). For example, stringent conditions are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% sodium dodecylsulfate (SDS), and 10% dextran sulfate at 42° C., with washes at 42° C. in 0.2×SSC and 0.1% SDS.

The term "end-product inhibition" refers to the reduction of enzymatic activity at a step in a synthetic pathway that is caused by accumulation of end-products of the pathway. For example, the activity of AK enzymes can be inhibited by lysine and/or threonine which are end products in a synthetic pathway involving AK. Thus, in certain aspects, AK enzymes described herein are enzymes that are not subject to end-product inhibition by lysine and/or threonine, meaning that end-products such as lysine and threonine have a reduced ability to inhibit AK activity (as compared inhibition of a wt AK enzyme). In certain cases, AK enzymes that are not subject to end-product inhibition by lysine or threonine exhibit reduced binding to lysine and/or threonine.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism or chimeric genes. A "transgene" is a gene that has been introduced into the genome by a transformation procedure.

"Coding sequence" or "structural gene" refers to a nucleotide sequence that encodes a specific amino acid sequence or a functional RNA (such as, for example, RNAs associated with ribosome structure or a transfer RNA (tRNA). "Regulatory sequences" or "regulatory genes" refer to nucleotide sequences located upstream (5' non-coding sequences), within, or downstream (3' non-coding sequences) of a coding sequence, and that influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence, which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg, *Biochemistry of Plants*, 15:1-82 (1989). It is further recognized in the art that the exact boundaries of regulatory sequences generally have not been completely defined, accordingly, nucleic acid fragments of varying lengths that are upstream of (i.e., 5' to) a coding sequence may have identical promoter activity.

Biomass refers to living and recently dead biological material that can be used as fuel or for industrial production. Most commonly, biomass refers to plant matter grown for use as biofuel, but it also includes plant or animal matter used for production of fibers, chemicals, food, and heat.

Enhanced vigor/biomass, as used herein, is a growth characteristic of a plant whereby there is an elevated, increased or greater size of plant material above ground after seed germination as compared to the size of plant material found in a wild-type plant cell, plant tissue, plant part or plant, i.e., one where the genome has not been altered by the presence of an exogenous nucleic acid. For example, enhanced vigor can be demonstrated in transgenic plants by taller, fuller, leafier and darker green plant parts that that of wild-type plants.

End-product inhibition is a regulation of activity of a cellular metabolite or product by a downstream metabolite or product in a metabolic pathway.

The term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A replicon is a DNA molecule or RNA molecule, or a region of DNA or RNA, that replicates from a single origin of replication.

Transcriptionally active refers to the capability of any polynucleotide molecule of being transcribed into a RNA molecule. Methods are known for introducing constructs into a cell in such a manner that the transcribable polynucleotide molecule is transcribed into a functional mRNA molecule that is translated and therefore expressed as a protein product. Such a polynucleotide molecule would be understood to be transcriptionally active.

Essential amino acids are those amino acids that cannot be synthesized de novo by the organism and therefore must be supplied in the diet.

Free amino acids are those amino acids that are not bound to other cell components including, but not limited to, proteins, cell wall constituents, and organelles.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The present invention relates to novel nucleic acids and methods for obtaining plants that produce elevated levels of free threonine. The overproduction results from the introduction and expression of a nucleic acid encoding a modified aspartate kinase.

Native plant aspartate kinases are generally quite sensitive to feedback inhibition by lysine. Such inhibition constitutes a key mechanism for regulating the threonine synthetic pathway. Therefore, an aspartate kinase that is highly active, more efficient or that is inhibited to a lesser extent by lysine will likely produce elevated levels of threonine. According to the invention, the modified *Xenorhabdus bovienii* aspartate kinase is particularly useful for producing high levels of threonine.

To generate high levels of threonine in a plant or a selected host cell, the selected aspartate kinase nucleic acid is isolated and may be manipulated in vitro to include regulatory signals required for gene expression in plant cells or other cell types. Because the threonine biosynthetic pathway in plants is reported to be present within plastids, the exogenous aspartate kinase nucleic acids are either introduced into plastids or are modified by adding a nucleic acid segment encoding an amino-terminal plastid transit peptide. Such a plastid transit peptide can direct the aspartate kinase gene product into plastids. In some instances the aspartate kinase may already contain a plastid transport sequence, in which case there is no need to add one.

In order to alter the biosynthesis of threonine, the nucleic acid encoding an aspartate kinase activity must be introduced into plant cells or other host cells and these transformed cells identified, either directly or indirectly. An entire aspartate kinase or a useful portion thereof can be used. The aspartate kinase is stably incorporated into the plant cell genome. The transcriptional signals controlling expression of the aspartate kinase must be recognized by and be functional within the plant cells or other host cells. That is, the aspartate kinase must be transcribed into messenger RNA (mRNA), and the mRNA must be stable in the plant cell nucleus and be transported intact to the cytoplasm for translation. The aspartate kinase mRNA must have appropriate translational signals to be recognized and properly translated by plant cell ribosomes. The polypeptide gene product must substantially escape proteolytic attack in the cytoplasm, be transported into the correct cellular compartment (e.g. a plastid) and be able to assume a three-dimensional conformation that will confer enzymatic activity. The aspartate kinase must further be able to function in the biosynthesis of threonine and its derivatives; that is, it must be localized near the native plant enzymes catalyzing the flanking steps in biosynthesis (presumably in a plastid) in order to obtain the required substrates and to pass on the appropriate product.

Even if all these conditions are met, successful overproduction of threonine is not a predictable event. The expression of some transgenes may be negatively affected by nearby chromosomal elements. If the high level of threonine is achieved by modification to reduce feedback inhibition, there may be other control mechanisms compensating for the reduced regulation at the aspartate kinase step. There may be mechanisms that increase the rate of breakdown of the accumulated amino acids. Threonine and related amino acids must be also overproduced at levels that are not toxic to the plant. Finally, the introduced trait must be stable and heritable in order to permit commercial development and use.

Nucleic acids encoding an aspartate kinase can be identified and isolated by standard methods, for example, as described by Sambrook et al., (1989); Sambrook and Russell, (2001). For example, a DNA sequence encoding an aspartate kinase or a domain thereof can be identified by screening of a DNA or cDNA library generated from nucleic acid derived from a particular cell type, cell line, primary cells, or tissue. Moreover, aspartate kinase nucleic acids can be isolated by nucleic acid amplification procedures using genomic DNA, mRNA or cDNA isolated from any of these species.

Screening for DNA fragments that encode all or a portion of the sequence encoding an aspartate kinase can be accomplished by screening plaques from a genomic or cDNA library for hybridization to a probe of an aspartate kinase gene from other organisms or by screening plaques from a cDNA expression library for binding to antibodies that specifically recognize aspartate kinase. DNA fragments that hybridize to aspartate kinase probes from other organisms and/or plaques carrying DNA fragments that are immunoreactive with antibodies to aspartate kinase can be subcloned into a vector and sequenced and/or used as probes to identify other cDNA or genomic sequences encoding all or a portion of the desired aspartate kinase gene.

A cDNA library can be prepared, for example, by random oligo priming or oligo dT priming. Plaques containing DNA fragments can be screened with probes or antibodies specific for aspartate kinase. DNA fragments encoding a portion of an aspartate kinase gene can be subcloned and sequenced and used as probes to identify a genomic aspartate kinase gene. DNA fragments encoding a portion of a bacterial or plant aspartate kinase can be verified by determining sequence homology with other known aspartate kinase genes or by hybridization to aspartate kinase-specific messenger RNA. Once cDNA fragments encoding portions of the 5', middle and 3' ends of an aspartate kinase are obtained, they can be used as probes to identify and clone a complete genomic copy of the aspartate kinase gene from a genomic library.

Portions of the genomic copy or copies of an aspartate kinase gene can be sequenced and the 5' end of the gene identified by standard methods including either by DNA sequence homology to other aspartate kinase genes or by RNAase protection analysis, for example, as described by Sambrook et al., (1989); (2001). The 3' and 5' ends of the target gene can also be located by computer searches of genomic sequence databases using known AS coding regions. Once portions of the 5' end of the gene are identified, complete copies of the aspartate kinase gene can be obtained by standard methods, including cloning or polymerase chain reaction (PCR) synthesis using oligonucleotide primers complementary to the DNA sequence at the 5' end of the gene. The presence of an isolated full-length copy of the aspartate kinase gene can be verified by hybridization, partial sequence analysis, or by expression of a maize aspartate kinase enzyme.

Site directed mutagenesis can be used to generate amino acid substitutions, deletions and insertions at a variety of sites. Examples of specific mutations made within the *Xenorhabdus bovienii* aspartate kinase coding region include the following:

at about position 257 replace Glu with Lys (see e.g., SEQ ID NOs: 1 and 4);

at about position 359 replace Thr with Ile (see e.g., SEQ ID NOs: 2, 3 and 4).

Similar modifications can be made in analogous positions of any aspartate kinase by alignment of the amino acid sequence of the aspartate kinase to be mutated with an *Xenorhabdus bovienii* aspartate kinase amino acid sequence. One example of an *Xenorhabdus bovienii* aspartate kinase amino acid sequence that can be used for alignment is SEQ ID NO: 4.

In general, expression of bacterial genes in plants may often result in inefficient protein accumulation. This can be attributed to suboptimal usage of amino acid codons in the host plant, resulting in limitation of some of the tRNAs corresponding to rare codons of the bacterial gene, presence of cryptic mRNA processing sites, or due to inefficient initiation of translation. The major block to efficient bacterial gene expression in plants appears to be at the translational level, as evidenced by low level expression of wild-type cry1A(b) and cry1A(c) genes in tobacco, tomato and cotton (Perlak et al., 1991). One of the efficient methods to optimize or to correct low levels of protein expression is to modify the transgene DNA sequence in accordance with the favorable codon usage preference of the host organism. In addition, modification of the regions that are A+T-rich resembling plant introns (Goodall and Filipowich, 1989) or potential polyadenylation signal sequences and mRNA splicing sites (Dean et al., 1986) may enhance the stability of the mRNA in the host organism.

Coding regions of any DNA molecule provided herein can also be optimized for expression in a selected organism, for example, a selected plant or other host cell type. An example of a DNA molecule having optimized codon usage for a selected plant is an *Xenorhabdus bovienii* aspartate kinase DNA molecule having SEQ ID NO: 3. This optimized *Xenorhabdus bovienii* aspartate kinase DNA (SEQ ID NO: 3) has 72.6% identity with SEQ ID NO: 2.

Once a nucleic acid encoding aspartate kinase is obtained and amplified, it is operably combined with a promoter and, optionally, with other elements to form a transgene.

Most genes have regions of DNA sequence that are known as promoters and which regulate gene expression. Promoter regions are typically found in the flanking DNA sequence upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous genes, that is, a gene different from the native or homologous gene. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue specific or developmental regulation. An isolated promoter sequence that is a strong promoter for heterologous genes is advantageous because it provides for a sufficient level of gene expression to allow for easy detection and selection of transformed cells and provides for a high level of gene expression when desired.

The promoter in a transgene of the present invention can provide for expression of aspartate kinase from a DNA sequence encoding aspartate kinase. Preferably, the coding sequence is expressed so as to result in an increase in threonine levels within plant tissues, for example, within the seeds of the plant. In another embodiment, the coding sequence is expressed so as to result in increased tolerance of the plant cells to feedback inhibition or to growth inhibition by lysine or so as to result in an increase in the total threonine content of the cells. The promoter can also be inducible so that gene expression can be turned on or off by an exogenously added agent. For example, a bacterial promoter such as the $P_{tac}$ promoter can be induced to varying levels of gene expression depending on the level of isothiopropylgalactoside added to the transformed bacterial cells. It may also be preferable to combine the gene with a promoter that provides tissue specific expression or developmentally regulated gene expression in plants. Many promoters useful in the practice of the invention are available to those of skill in the art.

Preferred promoters will generally include, but are not limited to, promoters that function in bacteria, bacteriophage, plastids or plant cells. Useful promoters include the CaMV 35S promoter (Odell et al., 1985), the CaMV 19S (Lawton et al., 1987), nos (Ebert et al., 1987), Adh (Walker et al., 1987), sucrose synthase (Yang et al., 1990), α-tubulin, napin, actin (Wang et al., 1992), cab (Sullivan et al., 1989), PEPCase promoter (Hudspeth et al., 1989), maize L3 oleosin promoter, P-Zm.L3 (U.S. Pat. No. 6,433,252), USP99 promoter (U.S. Pat. No. 7,078,588), the 7S-alpha'-conglycinin promoter (Beachy et al., 1985), the 7Sα' promoter (U.S. Pat. No. 6,825,398) or those associated with the R gene complex (Chandler et al., 1989). Other useful promoters include the bacteriophage SP6, T3, and T7 promoters.

Plastid promoters can be also be used. Most plastid genes contain a promoter for the multi-subunit plastid-encoded RNA polymerase (PEP) as well as the single-subunit nuclear-encoded RNA polymerase. A consensus sequence for the nuclear-encoded polymerase (NEP) promoters and listing of specific promoter sequences for several native plastid genes can be found in Hajdukiewicz et al. (1997), which is hereby in its entirety incorporated by reference.

Examples of plastid promoters that can be used include the *Zea mays* plastid RRN (ZMRRN) promoter. The ZMRRN promoter can drive expression of a gene when the *Arabidopsis thaliana* plastid RNA polymerase is present. Similar promoters that can be used in the present invention are the *Glycine max* plastid RRN (SOYRRN) and the *Nicotiana tabacum* plastid RRN (NTRRN) promoters. All three promoters can be recognized by the *Arabidopsis* plastid RNA polymerase. The general features of RRN promoters are described by Hajdukiewicz et al. and U.S. Pat. No. 6,218,145.

Moreover, transcription enhancers or duplications of enhancers can be used to increase expression from a particular promoter. Examples of such enhancers include, but are not limited to, elements from the CaMV 35S promoter and octopine synthase genes (Last et al., U.S. Pat. No. 5,290,924). For example, it is contemplated that vectors for use in accordance with the present invention may be constructed to include the ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). It is proposed that the use of an enhancer element, such as the ocs element and particularly multiple copies of the element, will act to increase the level of transcription from adjacent promoters when applied in the context of monocot transformation. Tissue-specific promoters, including but not limited to, root-cell promoters (Conkling et al., 1990), and tissue-specific enhancers (Fromm et al., 1989) are also contemplated to be particularly useful, as are inducible promoters such as ABA- and turgor-inducible promoters, and the like.

As the DNA sequence between the transcription initiation site and the start of the coding sequence, i.e., the untranslated leader sequence, can influence gene expression, one may also wish to employ a particular leader sequence. Any leader sequence available to one of skill in the art may be employed. Preferred leader sequences direct optimum levels of expression of the attached gene, for example, by increasing or maintaining mRNA stability and/or by preventing inappropriate initiation of translation (Joshi, 1987). The choice of such sequences is at the discretion of those of skill in the art. Sequences that are derived from genes that are highly expressed in dicots, and in soybean in particular, are contemplated.

In some cases, extremely high expression of aspartate kinase is not necessary. For example, using the methods of the invention such high levels of aspartate kinase may be generated that the availability of substrate, rather than enzyme, may limit the levels of threonine generated. In such cases, more moderate or regulated levels of expression can be selected by one of skill in the art. Such a skilled artisan can readily modulate or regulate the levels of expression, for example, by use of a weaker promoter or by use of a developmentally regulated or tissue specific promoter.

Nucleic acids encoding the aspartate kinase of interest can also include a plastid transit peptide to facilitate transport of the aspartate kinase polypeptide into plastids, for example, into chloroplasts. A nucleic acid encoding the selected plastid transit peptide (e.g. SEQ ID NO: 13) is generally linked in-frame with the coding sequence of the aspartate kinase. However, the plastid transit peptide can be placed at either the N-terminal or C-terminal end of the aspartate kinase.

Constructs also include the nucleic acid of interest (e.g. DNA encoding an aspartate kinase) along with a nucleic acid sequence that acts as a transcription termination signal and that allows for the polyadenylation of the resultant mRNA. Such transcription termination signals are placed 3' or downstream of the coding region of interest. Preferred transcription termination signals contemplated include the transcription termination signal from the nopaline synthase gene of *Agrobacterium tumefaciens* (Bevan et al., 1983), the terminator from the octopine synthase gene of *Agrobacterium tumefaciens*, the 3'-UTR of the glutelin 1 gene of *Oryza sativa* (Os-gt1; SEQ ID NO: 148), and the 3' end of genes encoding protease inhibitor I or II from potato or tomato, although other transcription termination signals known to those of skill in the art are also contemplated. Regulatory elements such as Adh intron 1 (Callis et al., 1987), sucrose synthase intron (Vasil et al., 1989) or TMV omega element (Gallie et al., *The Plant Cell*, 1:301 (1989)) may further be included where desired. These 3' nontranslated regulatory sequences can be obtained as described in An (1987) or are already present in plasmids available from commercial sources such as Clontech, (Palo Alto, Calif.). The 3' nontranslated regulatory sequences can be operably linked to the 3 terminus of an aspartate kinase gene by standard methods. Other such regulatory elements useful in the practice of the invention are known to those of skill in the art.

A DNA construct may comprise a first expression cassette, comprised of, in operable linkage, a heterologous promoter, a DNA molecule encoding a modified aspartate kinase protein and a transcriptional terminator. This DNA construct may further comprise a second expression cassette in operable linkage, comprising a heterologous promoter, a DNA molecule encoding a second protein and a transcriptional terminator.

Selectable marker genes or reporter genes are also useful in the present invention. Such genes can impart a distinct phenotype to cells expressing the marker gene and thus allow such transformed cells to be distinguished from cells that do not have the marker. Selectable marker genes confer a trait that one can "select" for by chemical means, i.e., through the use of a selective agent (e.g., a herbicide, antibiotic, or the like). Reporter genes, or screenable genes, confer a trait that one can identify through observation or testing, i.e., by "screening" (e.g., the R-locus trait). Of course, many examples of suitable marker genes are known to the art and can be employed in the practice of the present invention.

Possible selectable markers for use in connection with the present invention include, but are not limited to, a neo gene (Potrykus et al., 1985) which codes for neomycin resistance and can be selected for using kanamycin, G418, and the like; a bar gene which codes for bialaphos resistance; a gene which encodes an altered EPSP synthase protein (Hinchee et al., 1988) thus conferring glyphosate resistance; a nitrilase gene such as bxn from *Klebsiella ozaenae* which confers resistance to bromoxynil (Stalker et al., 1988); a mutant acetolactate synthase gene (ALS) that confers resistance to imidazolinone, sulfonylurea or other ALS-inhibiting chemicals (EP 154 204 (1985)); a methotrexate-resistant DHFR gene (Thillet et al., 1988); or a dalapon dehalogenase gene that confers resistance to the herbicide dalapon. Where a mutant EPSP synthase gene is employed, additional benefit may be realized through the incorporation of a suitable plastid transit peptide (CTP).

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes* (U.S. Pat. No. 5,550,318, which is incorporated by reference herein). The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) that encodes a catechol dioxygenase that can convert chromogenic catechols; an α-amylase gene (Ikuta et al., 1990); a tyrosinase gene (Katz et al., 1983) that encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., 1986), which allows for bioluminescence detection; or even an aequorin gene (Prasher et al., 1985), which may be employed in calcium-sensitive bioluminescence detection, or a green fluorescent protein gene (Niedz et al., 1995). The presence of the lux gene in transformed cells may be detected using, for example, X-ray film, scintillation counting, fluorescent spectrophotometry, low-light video cameras, photon-counting cameras, or multiwell luminometry. It is also envisioned that this system may be developed for population screening for bioluminescence, such as on tissue culture plates, or even for whole plant screening.

Additionally, transgenes may be constructed and employed to provide targeting of the gene product to an intracellular compartment within plant cells or in directing a protein to the extracellular environment. This will generally be achieved by joining a DNA sequence encoding a transit or signal peptide sequence to the coding sequence of a particular gene. The resultant transit, or signal, peptide will transport the protein to a particular intracellular, or extracellular destination, respectively, and may then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences may increase the accumulation of gene product.

A particular example of such a use concerns the direction of an aspartate kinase to a particular organelle, such as the plastid, rather than to the cytoplasm. This is exemplified by the use of the *Arabidopsis* SSU1A transit peptide that confers plastid-specific targeting of proteins. Alternatively, the transgene can comprise a plastid transit peptide-encoding DNA sequence or a DNA sequence encoding the rbcS (RuBISCO) transit peptide operably linked between a promoter and the DNA sequence encoding an aspartate kinase (for a review of plastid targeting peptides, see Heijne et al. (1989); Keegstra et al. (1989). If the transgene is to be introduced into a plant cell, the transgene can also contain plant transcriptional termination and polyadenylation signals and translational signals linked to the 3' terminus of a plant aspartate kinase gene.

An exogenous plastid transit peptide can be used which is not encoded within a native plant aspartate kinase gene. A plastid transit peptide is typically 40 to 70 amino acids in length and functions post-translationally to direct a protein to the plastid. The transit peptide is cleaved either during or just after import into the plastid to yield the mature protein. The complete copy of a gene encoding a plant aspartate kinase may contain a plastid transit peptide sequence. In that case, it may not be necessary to combine an exogenously obtained plastid transit peptide sequence into the transgene.

Exogenous plastid transit peptide encoding sequences can be obtained from a variety of plant nuclear genes, so long as the products of the genes are expressed as pre-proteins comprising an amino terminal transit peptide and transported into plastid. Examples of plant gene products known to include such transit peptide sequences include, but are not limited to, the small subunit of ribulose biphosphate carboxylase, chlorophyll a/b binding protein, plastid ribosomal proteins encoded by nuclear genes, certain heatshock proteins, amino acid biosynthetic enzymes such as acetolactate acid synthase, 3-enolpyruvylphosphoshikimate synthase, dihydrodipicolinate synthase, aspartate kinase and the like. In some instances a plastid transport protein already may be encoded in the aspartate kinase gene of interest, in which case there may be no need to add such plastid transit sequences. Alternatively, the DNA fragment coding for the transit peptide may be chemically synthesized either wholly or in part from the known sequences of transit peptides such as those listed above.

Regardless of the source of the DNA fragment coding for the transit peptide, it should include a translation initiation codon, for example, an ATG codon, and be expressed as an amino acid sequence that is recognized by and will function properly in plastids of the host plant. Attention should also be given to the amino acid sequence at the junction between the transit peptide and the aspartate kinase enzyme where it is cleaved to yield the mature enzyme. Certain conserved amino acid sequences have been identified and may serve as a guideline. Precise fusion of the transit peptide coding sequence with the aspartate kinase coding sequence may require manipulation of one or both DNA sequences to introduce, for example, a convenient restriction site. This may be accomplished by methods including site-directed mutagenesis, insertion of chemically synthesized oligonucleotide linkers, and the like.

Precise fusion of the nucleic acids encoding the plastid transport protein may not be necessary so long as the coding sequence of the plastid transport protein is in-frame with that of the aspartate kinase. For example, additional peptidyl or amino acids can often be included without adversely affecting the expression or localization of the protein of interest.

Once obtained, the plastid transit peptide sequence can be appropriately linked to the promoter and an aspartate kinase coding region in a transgene using standard methods. A plasmid containing a promoter functional in plant cells and having multiple cloning sites downstream can be constructed or obtained from commercial sources. The plastid transit peptide sequence can be inserted downstream from the promoter using restriction enzymes. An aspartate kinase coding region can then be translationally fused or inserted immediately downstream from and in frame with the 3' terminus of the plastid transit peptide sequence. Hence, the plastid transit peptide is preferably linked to the amino terminus of the aspartate kinase. Once formed, the transgene can be subcloned into other plasmids or vectors.

In addition to nuclear plant transformation, the present invention also extends to direct transformation of the plastid genome of plants. Hence, targeting of the gene product to an intracellular compartment within plant cells may also be achieved by direct delivery of a gene to the intracellular compartment. Direct transformation of plastid genome may provide additional benefits over nuclear transformation. For example, direct plastid transformation of aspartate kinase eliminates the requirement for a plastid targeting peptide and post-translational transport and processing of the pre-protein derived from the corresponding nuclear transformants. Plastid transformation of plants has been described by Maliga (2002); Heifetz (2000); Bock (2001); and Daniell et al. (2002), and other references cited and incorporated thereby within.

After constructing a transgene containing an aspartate kinase gene, the cassette can then be introduced into a plant cell. Depending on the type of plant cell, the level of gene expression, and the activity of the enzyme encoded by the gene, introduction of DNA encoding an aspartate kinase into the plant cell can lead to the overproduction of threonine, confer tolerance to lysine, and/or otherwise alter the threonine content of the plant cell.

A transgene comprising an aspartate kinase gene can be subcloned into a known expression vector, and AK expression can be detected and/or quantitated. This method of screening is useful to identify transgenes providing for an expression of an aspartate kinase gene, and expression of an aspartate kinase in the plastid of a transformed plant cell.

Plasmid vectors include additional DNA sequences that provide for easy selection, amplification, and transformation of the transgene in prokaryotic and eukaryotic cells, e.g., pUC-derived vectors, pSK-derived vectors, pGEM-derived vectors, pSP-derived vectors, or pBS-derived vectors. The additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the transgene, and sequences that enhance transformation of prokaryotic and eukaryotic cells.

Another vector that is useful for expression in both plant and prokaryotic cells is the binary Ti plasmid (Schilperoort et al., U.S. Pat. No. 4,940,838) as exemplified by vector pGA582. This binary Ti plasmid vector has been previously characterized by An, cited supra. This binary Ti vector can be replicated in prokaryotic bacteria such as E. coli and Agrobacterium. The Agrobacterium plasmid vectors can also be used to transfer the transgene to plant cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying a transgene of the invention can be used to transform both prokaryotic and eukaryotic cells, but is preferably used to transform plant cells. See, for example, Glassman et al., U.S. Pat. No. 5,258,300.

The expression vector can then be introduced into prokaryotic or eukaryotic cells by available methods. Methods of transformation especially effective for monocots and dicots, include, but are not limited to, microprojectile bombardment of immature embryos (U.S. Pat. No. 5,990,390) or Type II embryogenic callus cells as described by Gordon-Kamm et al. (1990); Fromm et al. (1990); Walters et al. (1992), or by electroporation of type I embryogenic calluses described by D'Halluin et al. (1992) or by Krzyzek (U.S. Pat. No. 5,384, 253). Transformation of plant cells by vortexing with DNA-coated tungsten whiskers (Coffee et al., U.S. Pat. No. 5,302, 523) and transformation by exposure of cells to DNA-containing liposomes can also be used.

Efficient selection of a desired lysine resistant, threonine-overproducer variant using tissue culture techniques requires careful determination of selection conditions. These conditions are optimized to allow growth and accumulation of lysine resistant, threonine overproducer cells in the culture while inhibiting the growth of the bulk of the cell population. The situation is complicated by the fact that the vitality of individual cells in a population can be highly dependent on the vitality of neighboring cells.

The choice of a selection protocol is dependent upon the considerations described above. The protocols briefly described below can be utilized in the selection procedure. For example, to select for cells that are resistant to growth inhibition by lysine, finely divided cells in liquid suspension culture can be exposed to high lysine levels for brief periods of time. Surviving cells are then allowed to recover and accumulate and are then re-exposed for subsequently longer periods of time. Alternatively, organized partially differentiated cell cultures are grown and subcultured with continuous exposure to initially low levels of lysine. Concentrations are then gradually increased over several subculture intervals. While these protocols can be utilized in a selection procedure, the present invention is not limited to these procedures.

As described herein above, genes that function as selectable marker genes and reporter genes can be operably combined with the DNA sequence encoding the aspartate kinase, or domain thereof, in transgenes, vectors and plants of the present invention. Additionally, other agronomical traits can be added to the transgenes, vectors and plants of the present invention. Such traits include, but are not limited to, insect resistance or tolerance; disease resistance or tolerance (viral, bacterial, fungal, nematode); stress resistance or tolerance, as exemplified by resistance or tolerance to drought, heat, chilling, freezing, excessive moisture, salt stress, oxidative stress, increased yields, food content and makeup, physical appearance, male sterility, dry down, standability, prolificacy, starch properties, oil quantity and quality, and the like. One may incorporate one or more genes conferring such traits into the plants of the present invention.

*Bacillus thuringiensis* (or "Bt") bacteria include nearly 20 known subspecies of bacteria which produce endotoxin polypeptides that are toxic when ingested by a wide variety of insect species. The biology and molecular biology of the endotoxin proteins (Bt proteins) and corresponding genes (Bt genes) has been reviewed by Whitely et al. (1986) and by Hofte et al. (1989). Genes coding for a variety of Bt proteins have been cloned and sequenced. A segment of the Bt polypeptide is essential for toxicity to a variety of Lepidoptera pests and is contained within approximately the first 50% of the Bt polypeptide molecule. Consequently, a truncated Bt polypeptide coded by a truncated Bt gene will in many cases retain its toxicity towards a number of Lepidoptera insect pests. For example, the HD73 and HD1 Bt polypeptides have been shown to be toxic to the larvae of the important Lepidoptera insect pests of plants in the U.S.A. such as the European corn borer, cutworms and earworms. The genes coding for the HD 1 and HD73 Bt polypeptides have been cloned and sequenced by Geiser et al. (1986) and Adang et al. (1985), respectively, and can be cloned from HD1 and HD73 strains obtained from culture collections (e.g. *Bacillus* Genetic Stock Center, Columbus, Ohio or USDA Bt stock collection Peoria, Ill.) using standard protocols. Examples of Bt genes and polypeptides are described, for example, in U.S. Pat. Nos. 6,329,574; 6,303,364; 6,320,100; and 6,331,655.

DNA coding for new, previously uncharacterized Bt toxins, may be cloned from the host *Bacillus* organism using protocols that have previously been used to clone Bt genes, and new synthetic forms of Bt toxins may also be produced.

A Bt gene useful in the present invention may include a 5' DNA sequence including a sequence of DNA which will allow for the initiation of transcription and translation of a downstream located Bt sequence in a plant. The Bt gene may also comprise a 3' DNA sequence that includes a sequence derived from the 3' non-coding region of a gene that can be expressed in the plant of interest. The Bt gene would also include a DNA sequence coding for a toxic Bt polypeptide produced by *Bacillus thuringiensis* or toxic portions thereof or having substantial amino sequence homology thereto. The Bt coding sequence may include: (i) DNA sequences which code for insecticidal proteins that have substantial homology to Bt endotoxins that are active against insect pests of the plant of interest, e.g., the HD73 or HD1 Bt sequences; (ii) sequences coding for insecticidally-active segments of the Bt endotoxin polypeptide, e.g., insecticidally active HD73 or HD1 polypeptides truncated from the carboxy and/or amino termini; and/or (iii) a truncated Bt sequence fused in frame with a sequence(s) that codes for a polypeptide that provides some additional advantage such as: (a) genes that are selectable, e.g., genes that confer resistance to antibiotics or herbicides, (b) reporter genes whose products are easy to detect or assay, e.g., luciferase or beta-glucuronidase; (c) DNA sequences that code for polypeptide sequences that have some additional use in stabilizing the Bt protein against degradation or enhance the efficacy of the Bt protein against insects, e.g., protease inhibitors; and (d) sequences that help direct the Bt protein to a specific compartment inside or outside the plant cell, e.g., a signal sequence.

To obtain optimum synthesis of a Bt protein or other heterologous protein in the plant, it may also be appropriate to adjust the DNA sequence of the gene encoding such a protein to more resemble the genes that are efficiently expressed in the plant of interest. Since the codon usage of Bt genes may be dissimilar to that used by genes that are expressed in the plant of interest, the expression of a Bt gene in plant cells may be improved by the replacement of codons with those that are more efficiently expressed in plants, e.g., are used more frequently in the plants of interest (See Murray et al., 1989). Such replacement of codons may require the substitution of bases without changing the amino acid sequence of the resulting Bt polypeptide. The Bt polypeptide may be identical in sequence to the bacterial gene or segments thereof. The complete Bt coding sequence, or sections thereof, containing a higher proportion of preferred codons than the original bacterial gene could be synthesized using standard chemical synthesis protocols, and introduced or assembled into the Bt gene using standard protocols, such as site-directed mutagenesis or DNA polymerization and ligation and the like.

Protease inhibitors may also provide insect resistance. For example, use of a protease inhibitor II gene, pinII, from tomato or potato may be useful. Also advantageous is the use of a pinII gene in combination with a Bt toxin gene. Other genes which encode inhibitors of the insects' digestive system, or those that encode enzymes or co-factors that facilitate the production of inhibitors, may also be useful. This group includes oryzacystatin and amylase inhibitors such as those from wheat and barley.

Genes encoding lectins may confer additional or alternative insecticide properties. (Murdock et al., 1990; Czapla and Lang, 1990. Lectin genes contemplated to be useful include, for example, barley and wheat germ agglutinin (WGA) and rice lectins. (Gatehouse et al., 1984).

Genes controlling the production of large or small polypeptides active against insects when introduced into the insect pests such as lytic peptides, peptide hormones and toxins and venoms, may also be useful. For example, the expression of juvenile hormone esterase, directed towards specific insect pests, may also result in insecticidal activity, or perhaps cause cessation of metamorphosis. (Hammock et al., 1990).

Transgenic plants expressing genes encoding enzymes that affect the integrity of the insect cuticle may also be useful. Such genes include those encoding, for example, chitinase, proteases, lipases and also genes for the production of nikkomycin. Genes that code for activities that affect insect molting, such those affecting the production of ecdysteroid UDP-glucosyl transferase, may also be useful.

Genes that code for enzymes that facilitate the production of compounds that reduce the nutritional quality of the plant to insect pests, may also be useful. It may be possible, for instance, to confer insecticidal activity to a plant by altering its sterol composition. Further embodiments of the present invention concern transgenic plants with enhanced lipoxygenase activity.

The introduction of genes that can regulate the production of maysin, and genes involved in the production of dhurrin in sorghum, is also contemplated to be of use in facilitating resistance to earworm and rootworm, respectively.

Further genes encoding proteins characterized as having potential insecticidal activity may also be used. Such genes include, for example, the cowpea trypsin inhibitor (CpTI; Hilder et al., 1987) which may be used as a rootworm deterrent; genes encoding avermectin (Campbell, 1989; Ikeda et al., 1987) which may prove useful as a corn rootworm deterrent; ribosome inactivating protein genes; and genes that regulate plant structures. Transgenic plants including anti-insect antibody genes and genes that code for enzymes that can convert a non-toxic insecticide (pro-insecticide) applied to the outside of the plant into an insecticide inside the plant are also contemplated.

Selections are carried out until cells or tissue are recovered which are observed to be growing well in the presence of normally inhibitory levels of a lysine. These cell "lines" are subcultured several additional times in the presence of abnormally high levels of lysine to remove non-resistant cells and then characterized. The amount of resistance that has been obtained is determined by comparing the growth of these cell lines with the growth of unselected cells or tissue in the presence of various concentrations of lysine. Stability of the resistance trait of the cultured cells may be evaluated by simply growing the selected cell lines in the absence of lysine for various periods of time and then analyzing growth after re-exposing the tissue to the lysine. The resistant cell lines may also be evaluated using in vitro chemical studies to verify that the site of action of the threonine is altered to a form that is less sensitive to inhibition by lysine.

Transient expression of an aspartate kinase gene can be detected and quantitated in the transformed cells. Gene expression can be quantitated by RT-PCR analysis, a quantitative Western blot using antibodies specific for the cloned aspartate kinase or by detecting enzyme activity in the presence of high levels of lysine. The tissue and subcellular location of the cloned aspartate kinase can be determined by immunochemical staining methods using antibodies specific for the cloned aspartate kinase or subcellular fractionation and subsequent biochemical and/or immunological analyses. Sensitivity of the cloned aspartate kinase to agents can also be assessed. Transgenes providing for expression of an aspartate kinase or aspartate kinase tolerant to inhibition by lysine can then be used to transform monocot and/or dicot plant tissue cells and to regenerate transformed plants and seeds. Transformed cells can be selected by detecting the presence of a selectable marker gene or a reporter gene, for example, by detecting a selectable herbicide resistance marker. Transient expression of an aspartate kinase gene can be detected in the transgenic embryogenic calli using antibodies specific for the cloned aspartate kinase, or by RT-PCR analyses.

Transformed embryogenic calli, meristematic tissue, embryos, leaf discs and the like can then be used to generate transgenic plants that exhibit stable inheritance of the transformed aspartate kinase gene. Plant cell lines exhibiting satisfactory levels of tolerance to high levels of lysine are put through a plant regeneration protocol to obtain mature plants and seeds expressing the tolerance traits by methods well known in the art (for example, see U.S. Pat. Nos. 5,990,390 and 5,489,520; and Laursen et al., (1994)). The plant regeneration protocol allows the development of somatic embryos and the subsequent growth of roots and shoots. To determine that the tolerance trait is expressed in differentiated organs of the plant, and not solely in undifferentiated cell culture, regenerated plants can be assayed for the levels of threonine present in various portions of the plant relative to regenerated, non-transformed plants. Transgenic plants and seeds can be generated from transformed cells and tissues showing a change in threonine content or in resistance to feedback inhibition by lysine using standard methods. It is especially preferred that the threonine content of the leaves or seeds is increased. A change in specific activity of the enzyme in the presence of inhibitory amounts of lysine can be detected by measuring enzyme activity in the transformed cells as described by Widholm (1972). A change in total threonine content can also be examined by standard methods as described by Jones et al. (1981).

Mature plants are then obtained from cell lines that are known to express the trait. If possible, the regenerated plants are self pollinated. In addition, pollen obtained from the regenerated plants is crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

The commercial value of threonine overproducer soybeans, cereals and other plants is greatest if different hybrid combinations are available for sale. The farmer typically grows more than one kind of hybrid based on such differences as maturity, standability or other agronomic traits. Additionally, hybrids adapted to one part of the country are not adapted to another part because of differences in such traits as maturity, disease, and insect resistance. Because of this, it is necessary to breed threonine overproduction into a large number of parental inbred lines so that many hybrid combinations can be produced.

A conversion process (backcrossing) is carried out by crossing the original overproducer line to normal elite lines and crossing the progeny back to the normal parent. Subsequent to the backcrossing, the new overproducer lines and the appropriate combinations of lines which make good commercial hybrids are evaluated for overproduction as well as a battery of important agronomic traits. Overproducer lines and hybrids are produced which are true to type of the original normal lines and hybrids. This requires evaluation under a range of environmental conditions where the lines or hybrids will generally be grown commercially. For production of high threonine soybeans, it may be necessary that both parents of the hybrid seed be homozygous for the high threonine character. Parental lines of hybrids that perform satisfactorily are increased and used for hybrid production using standard hybrid seed production practices.

The transgenic plants produced herein are expected to be useful for a variety of commercial and research purposes. Transgenic plants can be created for use in traditional agriculture to possess traits beneficial to the consumer of the grain harvested from the plant (e.g., improved nutritive content in human food or animal feed). In such uses, the plants are generally grown for the use of their grain in human or animal foods. However, other parts of the plants, including stalks, husks, vegetative parts, and the like, may also have utility, including use as part of animal silage, fermentation feed, biocatalysis, or for ornamental purposes.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the recombinant DNA may be transferred, e.g., from soybean cells to cells of other species, e.g., by protoplast fusion.

EXAMPLES

The following examples further illustrate the invention and are not intended to be limiting thereof. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Isolation and Cloning of Aspartate Kinase Genes

Figure 3:
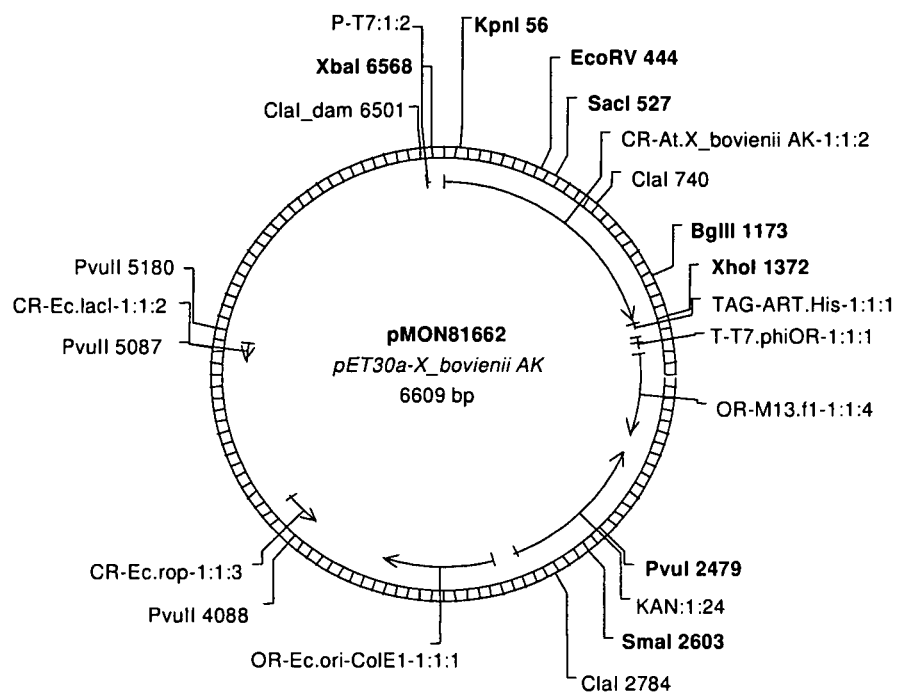
FIG. 3: pMON81662

The full-length coding sequence of the wild-type aspartate kinase gene was isolated by PCR amplification from 30 ng of *Xenorhabdus bovienii* genomic DNA using oligonucleotide primers SEQ ID NO: 11 and SEQ ID NO: 12. PCR was carried out in a total volume of 50 µL reaction mixture using the Expand™ High Fidelity PCR kit (Boehringer Mannheim, Germany). PCR conditions were as follows: one cycle of 4 min at 95° C.; 26 cycles of 1 min at 95° C., 1 min annealing at 56° C. and 2 min extension at 72° C.; one cycle of 7 min at 72° C. The resulting products were digested with appropriate restriction enzymes (NdeI and XhoI), gel purified, and ligated into the corresponding sites of pET30a (Novagen), yielding the plasmid pMON81662 (FIG. 3; XbAK) for expression of the recombinant protein. The gene sequence integrity was confirmed by DNA sequence analysis.

Example 2

Identification of Novel Aspartate Kinase Genes Encoding Variants with Desirable Enzymatic Properties This example describes the identification of AK genes that encode enzymes with desirable enzymatic properties, i.e., insensitivity to end-product inhibition by aspartate family amino acids and favorable kinetic properties. To characterize AK variants, recombinant expression systems and AK enzyme assays were established using the recombinant *E. coli* lysC and the *E. coli* T352I lysC (SEQ ID NO: 17) gene products as controls. The *E. coli* lysC gene product is known to be sensitive to feedback inhibition by Lys, whereas the *E. coli* T352I lysC gene product is known to be lysine-insensitive. Expression in plants of the *E. coli* T352I lysC gene product having aspartate kinase activity has resulted in a 6-7% increase in threonine content of the seed (Karchi, et al., THE PLANT J. 3:721-727 (1993); Galili, et al., European Patent Application No. 0485970). The lysC gene was cloned by PCR amplification using *E. coli* genomic DNA as template and PCR primers SEQ ID NO: 14 and SEQ ID NO: 15. Subsequently, the *E. coli* lysC and the *Xenorhabdus bovienii* AK genes were subjected to site-directed mutagenesis and cloned for recombinant protein production and/or for transformation into soy.

Site-directed mutagenesis was carried out to produce the E257K and T359I single variants as well as the E257K/T359I double variant of the *Xenorhabdus bovienii* AK gene using the following primers and conditions:

Primers used for PCR-based mutagenesis

| XbAKXhoIRv | (SEQ ID NO: 18) |
| XbAKNdeIFr | (SEQ ID NO: 19) |
| XbAKE257KFr | (SEQ ID NO: 20) |
| XbAKE257KRv | (SEQ ID NO: 21) |
| XbAKT359IFr | (SEQ ID NO: 22) |
| XbAKT359IRv | (SEQ ID NO: 23) |

PCR reactions were performed in a total volume of 50 μl using pMON81662 as a template.
1. For XbAK E257K,
    a) N-terminal piece (with primers XbAKNdeIFr and XbAKE257KRv). Expected product 797 bp.
    b) C-terminal piece (with primers XbAKXhoIRv and XbAKE257KFr). Expected product 624 bp.
2. For T359I,
    a) N-terminal piece (with primers XbAKNdeIFr and XbAKT359IRv). Expected product 1071 bp.
    b) C-terminal piece (with primers XbAKXhoIRv and XbAKT359IFr). Expected product 320 bp Reaction mixture per 100 μl contained: 83 μl water, 3 μl 10 mM dNTPs, 10 μl 10× ThermoPol buffer (NEB, for Vent), 2 μl DMSO, 1 μl plasmid template, 1 μl 100 μM forward primer, 1 μl 100 μM reverse primer, ~1 μl Vent DNA polymerase. Alternative mixture used AccuPrime™ Pfx DNA polymerase kit (Invitrogen).

Total reaction volume was 50 μl. A PTC-200 Peltier Thermal Cycler was set to the following program cycle:
2 min at 94° C.
24 cycles of [30 sec. at 94° C., 30 sec. at 50° C., 90 sec. at 72° C.]
5 min at 72° C.

50 μl of each PCR product was gel-purified on a 1.2% agarose-TAE gel. Purified product bands were cut from the gel and combined as follows:
a. For E257K, bands 1a and 1b from the above reactions were combined.
b. For T359I, bands 2a and 2b from the above reactions were combined.

The combined DNAs were eluted from the gel and recovered in ~35 μl of EB.

A second round of PCR reactions were set up as follows:
5 μl of mixture 1+2 or 3+4
1.5 μl 10 mM dNTPs
5 μl 10× ThermoPol buffer
1 μl DMSO
~0.5 μl Vent
+40 μl water The annealing and extension cycles were run without any added primers according to the following program cycle:
2 min at 94° C.
5 cycles of [30 sec. at 94° C., 30 sec. at 50° C., 75 sec. at 72° C.]
2 min at 72° C.

PCR was interrupted briefly to add 1.5 μl of XbAKXhoIRv and XbAKNdeIFr. The reaction was restarted using a slightly modified program:
2 min at 94° C.
24 cycles of [30 sec. at 94° C., 30 sec. at 50° C., 90 sec. at 72° C.]
5 min at 72° C.

The PCR products were then digested with NdeI and XhoI and cloned into a pET30a (Novagen) vector. The plasmids were identified by site restriction analysis and confirmed to carry the desired mutation by DNA sequencing. The plasmids were then transformed into *E. coli* BL21(DE3) for production of N-terminal His-tagged AK proteins. A list of vectors containing different AK sequences and controls generated as part of the AK biochemical characterization efforts are listed in Table 1.

Characterization of Aspartate Kinase Variants

Figure 4:
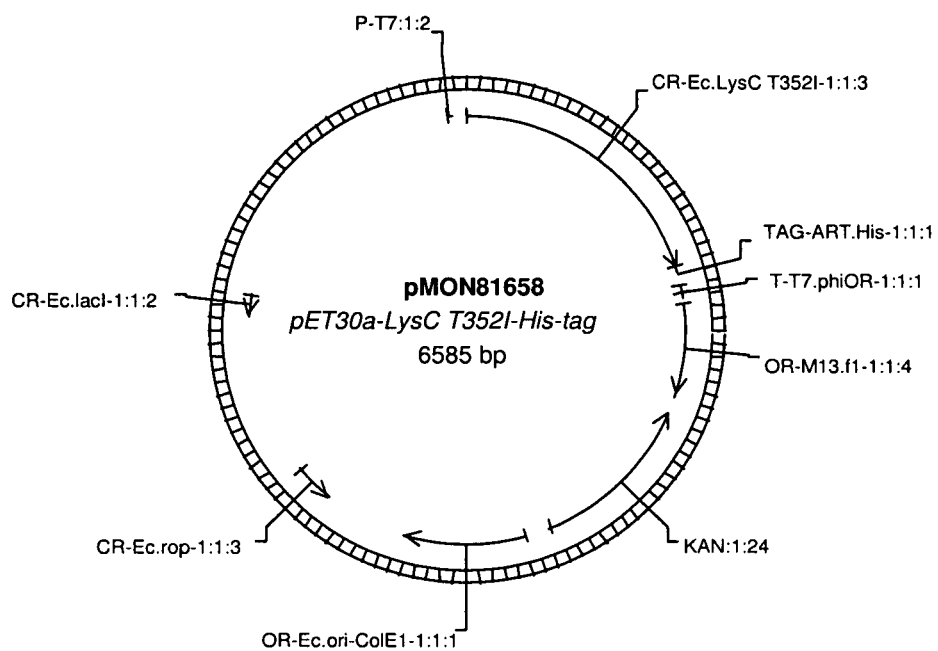
FIG. 4: pMON81658
Figure 5:
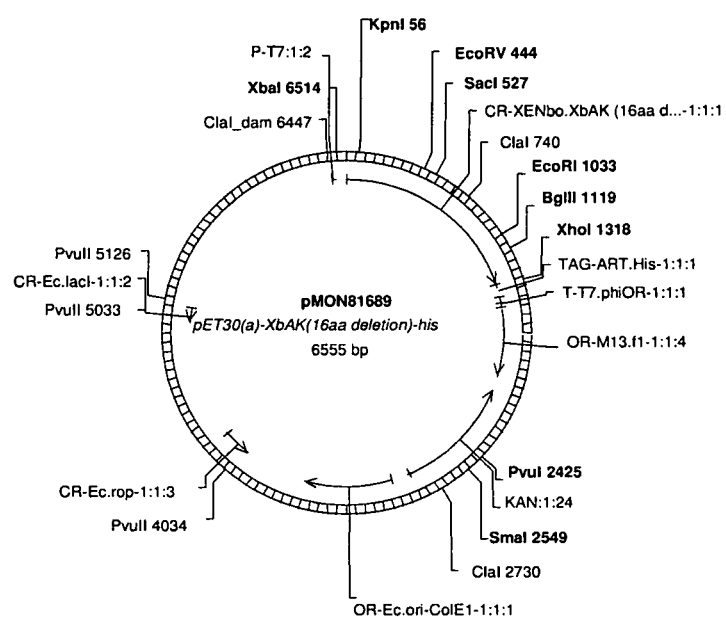
FIG. 5: pMON81689
Figure 6:
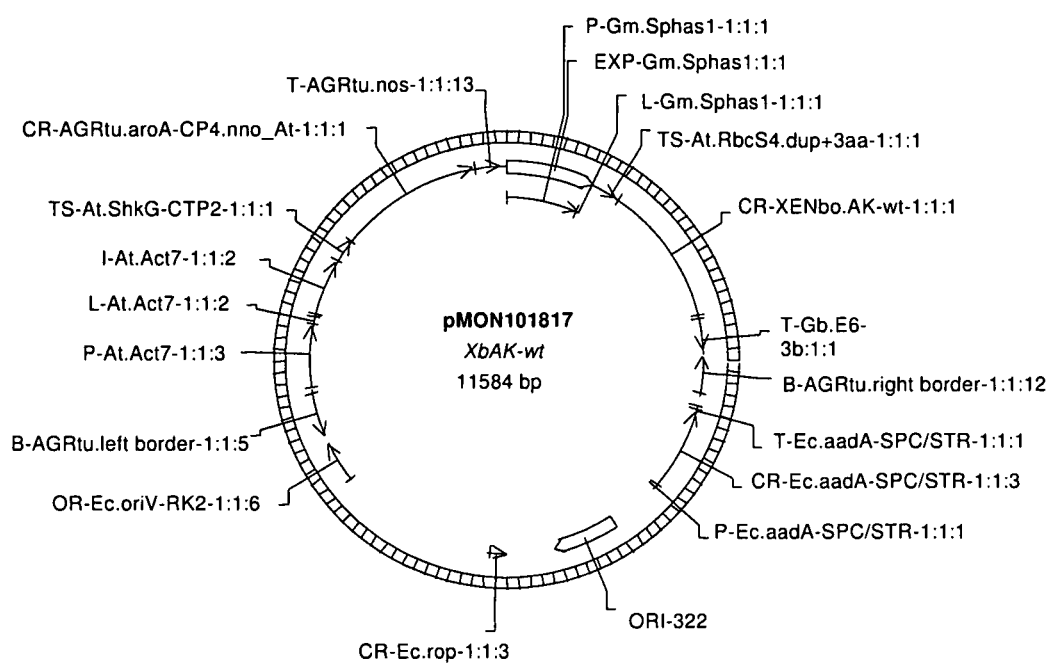
FIG. 6: pMON101817
Figure 7:
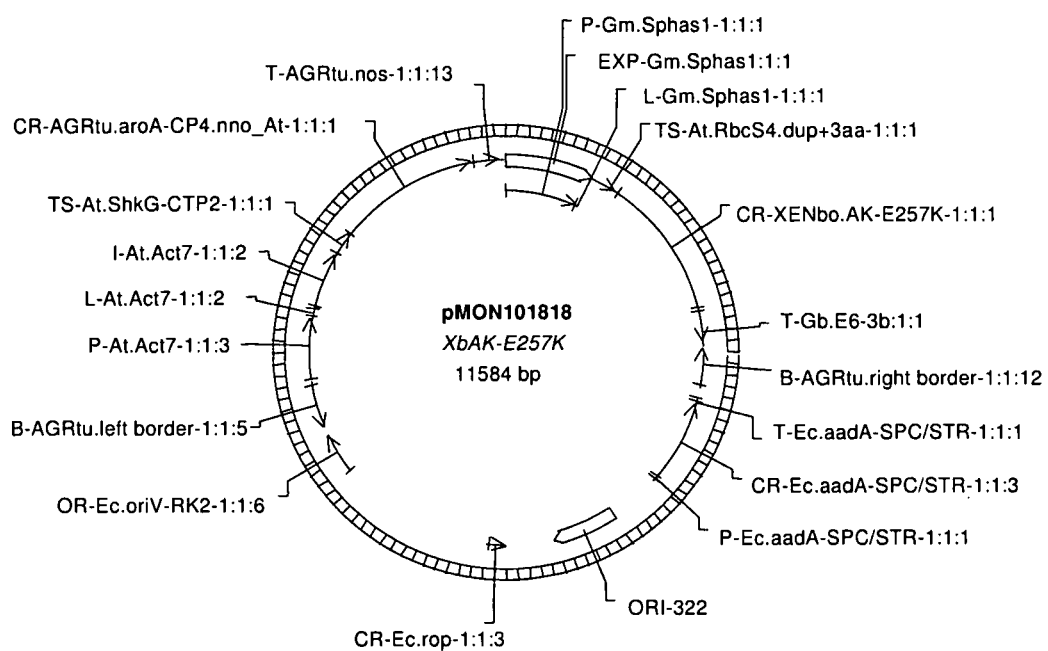
FIG. 7: pMON101818
Figure 8:
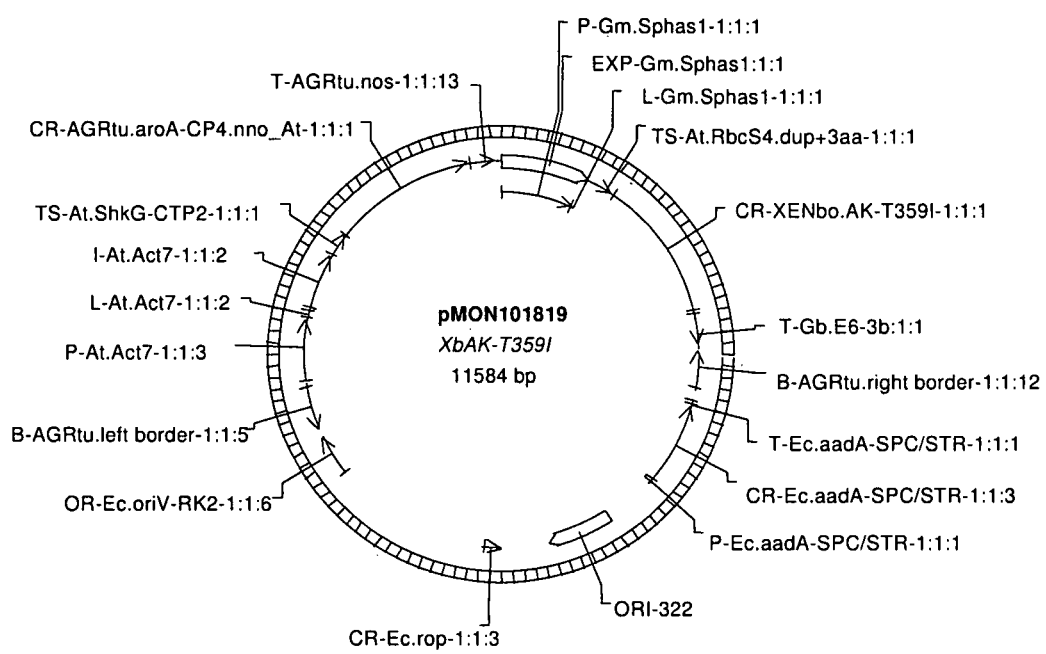
FIG. 8: pMON101819
Figure 9:
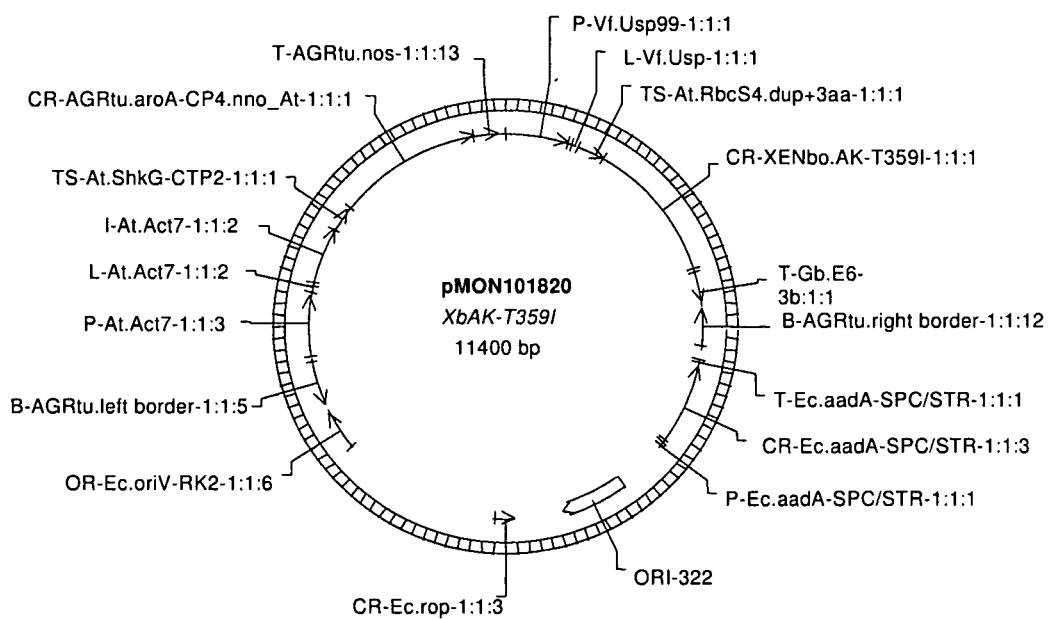
FIG. 9: pMON101820
Figure 10:
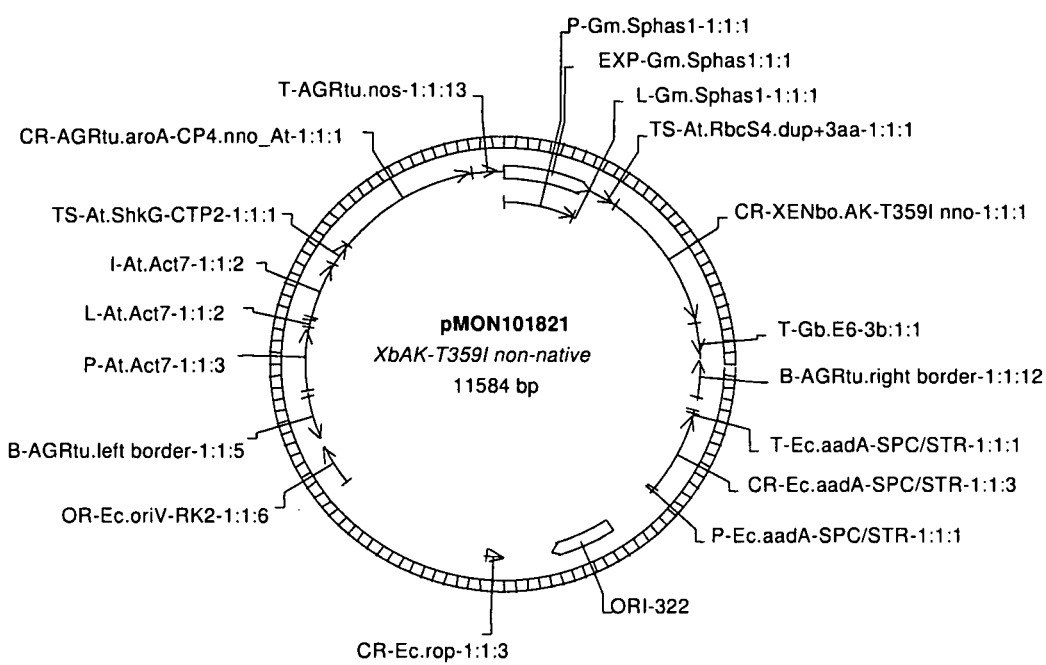
FIG. 10: pMON101821
Figure 11:
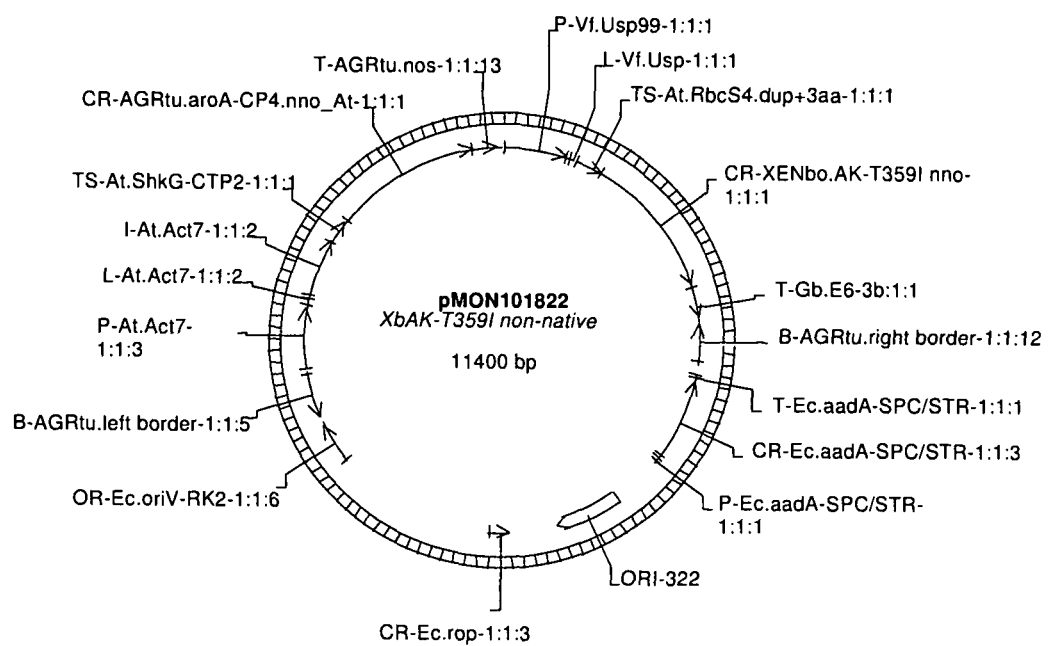
FIG. 11: pMON101822

The enzymatic properties of these *Xenorhabdus bovienii* aspartate kinase gene variants were characterized and compared to a previously studied *E. coli* lysC mutant allele (SEQ ID NO: 16; FIG. 4; pMON81658). To characterize AK variants, recombinant expression systems and AK enzyme assays were established using the recombinant *E. coli* lysC gene product.

The chimeric plasmids containing AK or the desired mutants were transformed into *E. coli* BL21 (DE3) cells and transformants were selected on LB (Luria-Bertani) medium containing kanamycin (50 μg/mL). For induction of gene expression, transformants selected from single colonies were grown in 100 mL liquid LB supplemented with ampicillin or kanamycin to approximately 0.6 $A_{600}$, and 0.4 mM. Isopropyl-β-thiogalactopyranoside (IPTG) (Gold Biotechnologies, St. Louis, Mo.) was added, followed by 15 hours incubation at 21° C. and 220 rpm shaking. Cells were harvested by 30 min centrifugation at 7,000×g and washed once with 20 mM Tris-HCl, 150 mM NaCl, pH 7.4. Washed cell pellets were re-suspended in 50 mM K-phosphate buffer (pH7.4, Buffer A) containing 2 mM $MgCl_2$, 50 mM NaCl, 100 units of benzonase (Novagen, San Diego, Calif.) and protease inhibitor cocktail tablets without EDTA (1 tablet/10 mL) (Boehringer Mannheim, Germany). Cells were broken by three passages through a chilled French press cell (SLM-Aminco Spectronic Instruments), operating at 20,000 psi. The lysate was centrifuged by an ultra-centrifuge for 1 hour at 100,000×g, at 4° C.

The resulting supernatant was applied to nickel+-nitrilotriacetic acid (Ni+NTA) agarose column (His-Bind resin, Qiagen) and chromatographed according to the supplier's instructions. The column was washed with 3 bed volumes of Buffer A containing 20 mM imidiazole followed by elution with 300 mM imidazole. Enzymatically active fractions of the N-terminal His-tagged GS2 were pooled, dialyzed against Buffer A without benzonase, and stored in 15% glycerol solution at −80° C. for use in kinetic studies. The enzyme preparation was over 95% pure as judged by Coomassie Blue-stained SDS-PAGE.

Enzyme Assays and Kinetic Studies

Colorimetric Hydroxamate Method. The assay mixture (final volume, 0.8 mL) contained 100 Tris-HCl, pH8.0, 40 mM hydroxylamine-KOH, pH8.0, 25 mM ATP-KOH, pH8.0, 20 mM MgCl$_2$, L-aspartic acid, and 150 mM KCl. The reaction was initiated by addition of AK enzyme, and carried out at 37° C. for 15-30 min. The reaction was terminated by addition of 400 μL acidified ferric chloride (0.37 M FeCl$_3$, 20% TCA, and 0.72 M HCl) and followed by the centrifugation at top speed of microcentrifuge. The formed aspartyl-hydroxamate was determined by colorimetrically at 505 nm. The biosynthetic activity was calculated based on the standard curves of L-aspartyl-hydroxamate or $\epsilon_{505nm}$.

A Coupled Assay Method.

The assay couples the conversion of ATP to ADP to the oxidation of NADH using pyruvate kinase and lactate dehydrogenase at 30° C. NADH oxidation was monitored kinetically at 340 nm. (See Wampler D E, Westhead E W. (1968), BIOCHEMISTRY 7: 1661-1670.)

Kinetics.

Kinetic parameters were determined by measuring product formation in 100 μL reaction mixtures containing various substrate concentrations ranging from 0 to 25 mM. Controls were included for every assay. Values for $K_m$, $V_{max}$, and $K_{cat}$ were calculated from the rate of the product formation using Michaelis-Menten equations in conjunction with the curve fitting options in the Grafit 5.0 software (Erithacus software Ltd., Horley, UK) (Table 2).

TABLE 1

Aspartate kinase vectors for expression in *E. coli*.

| pMON# | Coding region | Purpose | Comment |
|---|---|---|---|
| 81655 | MEA::lysC::His-tag | Kinetics study | Sensitive to Lys |
| 81656 | lysC::His-tag | Kinetics study | Sensitive to Lys |
| 81657 | His-tag::lysC | Kinetics study | Sensitive to Lys |
| 81658 | lysC T352I::His-tag | Kinetics study | Insensitive to Lys |
| 81662 | *X. bovienii* AK (XbAK)::His-tag | Kinetics study and antibody | Sensitive to Lys |
| 81665 | XbAK E257K::His-tag | Kinetics study | Insensitive to Lys |
| 81666 | XbAK T359I::His-tag | Kinetics study | Insensitive to Lys |
| 81667 | XbAK E257K/T359I::His-tag | Kinetics study | Insensitive to Lys |
| 81668 | XbAK T359I | *E. coli* complementary assay | Insensitive to Lys |
| 81669 | XbAK E257K/T359I | *E. coli* complementary assay | Insensitive to Lys |
| 81670 | XbAK E257K | *E. coli* complementary assay | Insensitive to Lys |
| 81675 | XnAK T359I | Kinetics study | Insensitive to Lys |
| 81689 | XbAK_16 aa deletion from position #345 to 361 | Mapping Lys-binding site | Insensitive to Lys, but remains 75% of Wt XbAK activity |

Thirteen *E. coli* expression vectors harboring aspartate kinase (AK) sequences were constructed for studies on kinetic properties, mutagenesis and feedback inhibition as well as antibody production.

TABLE 2

Kinetic properties for the purified *X. bovienii* aspartate kinase

| | $K_m$ Asp mM | $K_m$ ATP mM | $IC_{50}$ Lys mM | $V_{max}$ Asp μmoles · min$^{-1}$ · mg$^-$ | $K_{cat}/K_m$ Asp M$^{-1}$·S$^{-1}$ | $K_{cat}/K_m$ ATP M$^{-1}$·S$^{-1}$ |
|---|---|---|---|---|---|---|
| *X. bovienii* AK Wild Type | 2.73 | 2.56 | 0.14 | 0.29 | 27 × 10$^4$ | 31 × 10$^4$ |
| *X. bovienii* AK T359I | 2.31 | 1.82 | 145.4 | 0.26 | 29 × 10$^4$ | 37 × 10$^4$ |
| *X. bovienii* AK E257K | 3.06 | 1.89 | 121.5 | 0.20 | 4.4 × 10$^4$ | 11 × 10$^4$ |
| *X. bovienii* AK E257K/T359I | 3.10 | 1.62 | 187.2 | 0.24 | 12 × 10$^4$ | 17 × 10$^4$ |

Example 3

Construction of Soy Transformation Vectors Containing Feedback-Insensitive Aspartate Kinase Coding Sequences and Transformation into Soybean Plants Six soy transformation vectors were constructed, containing wild-type and mutant alleles of the *X. bovienii* AK genes (listed in Table 3), and these vectors were transformed into soybean.

TABLE 3

Soy transformation vectors containing aspartate kinase coding sequences

| pMON Number | Coding Region |
|---|---|
| pMON101817 | CTP1-*X. bovienii* AK |
| pMON101818 | CTP1-*X. bovienii* AK E257K |
| pMON101819 | CTP1-*X. bovienii* AK T359I |
| pMON101820 | CTP1-*X. bovienii* AK T359I |
| pMON101821 | CTP1-*X. bovienii* AK T359I-non-native |
| pMON101822 | CTP1-*X. bovienii* AK T359I-non-native |

The coding sequence for CTP1 (SEQ ID NO: 13) was incorporated at the N-terminus of the bacterial proteins in order to target the protein to the plastids in developing seeds. Targeting of the *E. coli* and *Arabidopsis* proteins as GFP fusions was evaluated in soybean and *Arabidopsis* protoplasts and the results are described in US patent publication US2008/050506A1. In general, constructs with chloroplast-targeting sequences were efficiently targeted to chloroplasts.

Soybean meristem tissues were excised from the embryos of germinated A3525 seed. After co-culturing with the *Agrobacterium tumefaciens* strain ABI carrying a vector chosen from Table 3, the meristems were placed on selection medium containing glyphosate and antibiotics to inhibit the growth of untransformed plant cells and excess *Agrobacterium*, respectively.

Plants were grown in a randomized block design in a greenhouse in 8 inch pots filled with Metro Mix 350 soil media with Peter's Pete Lite 15-16-17 liquid fertilizer applied at a rate of 1.0 mS. Mature seed was produced and analyzed for free amino acid content. Controls were included to establish base-line free amino acid levels, i.e. the corresponding negative isolines and the nontransgenic controls.

Example 4

Determination of R1 Seed Free Amino Acid Levels in Transgenic Aspartate Kinase Variant and Wild-Type Populations of Soybean Plants This example describes methods used for determining free amino acid levels in R1 seed of transgenic events containing the wild-type and feedback-resistant aspartate kinase genes from *Xenorhabdus bovienii*. Seed from each $R_0$ plant was bulked and 25 seeds were ground and analyzed for total free amino acids as described below. Results of those studies are reported below in Table 4.

In general, seed samples were ground, free amino acids were extracted with 5% (v/v) trichloroacetic acid (TCA) and the extracts were derivatized with o-pthaldialdehyde (OPA) to form fluorescent derivatives of all free amino acids except proline and cysteine. The amino acid derivatives were separated by reverse-phase high-pressure liquid chromatography (HPLC) and measured quantitatively using a fluorescence detector. The limit of detection (LOD) and the limit of quantitation (LOQ) are 5 and 10 ppm for each of the 18 amino acids, respectively.

Specifically, samples of 25 seeds were ground using a Mega-Grinder into a fine homogeneous powder. Approximately 30±5 mg of each ground sample was weighed and placed into each tube well of a Matrix Screen Mates Disposable tube rack (96×1.4 ml tubes per rack). 1.0 ml of 5% TCA was added to each sample; and tube wells were capped firmly and placed on a Vortex mixer for 30 minutes. Samples were incubated overnight at 4° C. to ensure complete extraction. The following day, samples were mixed on a Vortex mixer for 30 minutes. Samples were then centrifuged for 20 minutes at 3000 rpm and approximately 400.0 µl of the supernatant liquid was transferred into an 800 µl 96 well unifilter plate and filtered into a 1 ml 96 well mother plate in an Eppendorf centrifuge. Approximately 100 µl of the sample from the mother plate was transferred into a 350 µl 96 well daughter plate. The mother plate was stored in a −80° C. freezer. The daughter plate was positioned in an autosampler of HPLC for analysis. A checking standard was analyzed after every 10-sample injection to ensure that the HPLC was functioning properly.

The amino acids were separated by reverse-phase high-pressure liquid chromatography on a Zorbax Eclipse XDB-$C_{18}$ column (4.6×75 mm, 3.5 µm, Agilent) fitted with a Kromasil (Xpertek,) $C_{18}$ guard column (3×15 mm, 5 µm). The column compartment was set to maintain 40±0.8° C. The binary mobile phase system included 40 mM $NaH_2PO_4$ (pH 7.8) with 0.001% sodium azide as solvent A, and acetonitrile:methanol:$H_2O$ (45:45:10 v/v) as solvent B. All solvents were HPLC grade.

The twelve-minute HPLC run used a mobile phase flow rate of 2 mL/min with an initial solvent A to solvent B ratio of 95:5 hold for 1 min followed by a linear increase in solvent B to 35% at 9.80 min, then 100% at 12 min. Pre-column derivatization of amino acids to their OPA derivatives was performed by an injection program that exposes sample to OPA just prior to column loading. The resulting amino acid adducts were detected by a fluorescence detector (excitation 340 nm, emission 450 nm). Cysteine and proline were not included in this amino acid screen. A checking standard was analyzed after every 10-sample injection to ensure that the HPLC was functioning properly.

TABLE 4

Total free amino acid (FAA) levels were increased by up to 3-fold in transgenic soybean R1 seed populations containing feedback-resistant AK genes.

| | | Total FAA Level (ppm) | | |
| --- | --- | --- | --- | --- |
| Vector | Number of Events | Best Performing Event | Mean of All Events | Significance* |
| pMON101817 | 20 | 14553 | 8596.6 | A |
| pMON101818 | 14 | 16365 | 11584.5 | B |
| pMON101819 | 15 | 20209 | 13163.1 | C |
| pMON101820 | 11 | 21038 | 14196.9 | D |
| pMON101821 | 6 | 15343 | 12583.9 | C |
| pMON101822 | 13 | 15775 | 12999.1 | C |
| WT, A3525 | 26 | 6435 | 5530.2 | E |

*Significance was calculated using Tukey-Kramer HSD (JMP 6.0, SAS Institute) and means followed by the same letters are not significantly different from one another.

All four constructs containing the seed-expressed feedback-resistant forms of the *X. bovienii* aspartate kinase showed substantial increases in free threonine, with events from multiple constructs well exceeding the 31 ppm level in the A3525 control seed (Table 5). Seed from each $R_0$ plant was bulked and 25 seeds were ground and analyzed for total free threonine (ppm) according to the methods described above.

TABLE 5

R1 seed threonine levels were increased by up to 100-fold in transgenic soybean seed populations compared to that of wild-type seed populations.

| | | Threonine level (ppm) | | |
| --- | --- | --- | --- | --- |
| Vector | Number of Events | Best Performing Event | Mean of All Events | Significance* |
| pMON101817 | 20 | 68 | 37.5 | A |
| pMON101818 | 14 | 2882 | 538.5 | B |
| pMON101819 | 15 | 2999 | 1693.7 | C |
| pMON101820 | 11 | 3112 | 2142.2 | D |
| pMON101821 | 6 | 3048 | 1857.7 | E |
| pMON101822 | 13 | 3106 | 1807.9 | E |
| WT, A3525 | 26 | 31 | 23.3 | A |

*Significance was calculated using Tukey-Kramer HSD (JMP 6.0, SAS Institute) and means followed by the same letters are not significantly different from one another.

Changes were also observed in other aspartate-derived amino acids. These changes in transgenic events included significant increases in serine, methionine, glycine, and isoleucine, in addition to a decrease in aspartate (Table 6).

TABLE 6

Free amino acid (FAA) profiles in transgenic soybean R1 seed populations (Data represent the mean ppm calculated from all events in a construct).

| Vector | pMON101817 | pMON101818 | pMON101819 | pMON101820 | pMON101821 | pMON101822 | WT A3525 |
|---|---|---|---|---|---|---|---|
| Ala | 68 | 81 | 94 | 91 | 103 | 109 | 117 |
| Arg | 5098 | 4734 | 5103 | 5431 | 4231 | 4927 | 3208 |
| Asn | 1203 | 1501 | 2044 | 1998 | 1869 | 2045 | 342 |
| Asp | 811 | 733 | 404 | 414 | 377 | 384 | 614 |
| Glu | 713 | 823 | 786 | 799 | 933 | 812 | 496 |
| Gln | 15 | 21 | 33 | 24 | 24 | 21 | 14 |
| Gly | 39 | 106 | 269 | 269 | 269 | 243 | 43 |
| His | 76 | 94 | 152 | 126 | 135 | 171 | 106 |
| Ile | 81 | 98 | 120 | 117 | 139 | 109 | 40 |
| Leu | 38 | 45 | 52 | 41 | 58 | 43 | 32 |
| Lys | 75 | 113 | 233 | 261 | 228 | 195 | 99 |
| Met | 32 | 59 | 107 | 93 | 146 | 94 | 24 |
| Phe | 37 | 40 | 39 | 35 | 38 | 36 | 27 |
| Ser | 48 | 592 | 1780 | 2116 | 1949 | 1812 | 68 |
| Trp | 162 | 150 | 151 | 199 | 143 | 138 | 224 |
| Val | 62 | 64 | 101 | 42 | 57 | 46 | 51 |

Example 5

Determination of Shoot Biomass in Transgenic Aspartate Kinase Variant and Wild-Type Populations of Soybean Plants Thirty R1 seeds from each of 4 events of pMON101817, pMON101818, pMON101819, pMON101820, pMON101822, and 90 wild-type A3525 seeds were grown in a greenhouse until V1. The total number of germinated seeds from each event were counted and the germination rate was calculated in comparison with the wild-type total germinated seeds. Twenty shoots from each event and wild-type 10-day above ground seedlings were pooled and weighed.

Figure 12:
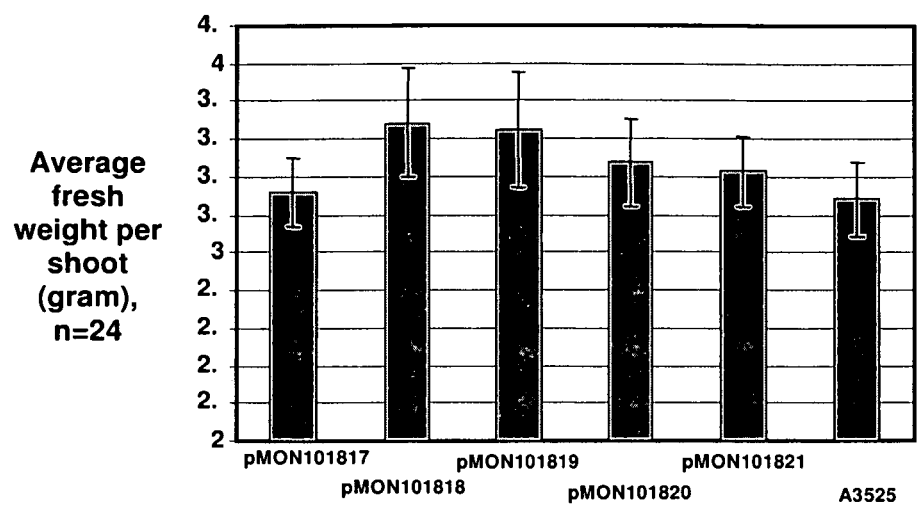
FIG. 12: Graphic depiction of increased shoot biomass in transgenic seedlings expressing *Xenorhabdus bovienii* aspartate kinase variant sequences

A photographic record was kept of transgenic plants from high threonine and serine seeds and wild-type plants at 7 and 14 days after planting. Serine and threonine levels for each event and wild-type seeds are reported in Table 7. Seedlings expressing the *Xenorhabdus bovienii* modified AK genes showed substantially increased shoot biomass. Average fresh weight per shoot (in grams) is provided in the graph at FIG. 12.

TABLE 7

*Xenorhabdus bovienii* AK mutant events and wild-type seeds for planting

| Serial Number | Construct | Event | Ser | Thr |
|---|---|---|---|---|
| 63010441157 | pMON101817 | GM_A166611 | 86 | 68 |
| 63010440460 | pMON101817 | GM_A166589 | 36 | 63 |
| 63010441006 | pMON101817 | GM_A166590 | 62 | 51 |
| 63010440939 | pMON101817 | GM_A166599 | 29 | 51 |
| 63010440559 | pMON101818 | GM_A166622 | 2496 | 2887 |
| 63010441094 | pMON101818 | GM_A166631 | 2925 | 2389 |
| 63010440674 | pMON101818 | GM_A166615 | 2034 | 2083 |
| 63010441208 | pMON101818 | GM_A166641 | 54 | 50 |
| 63010440838 | pMON101819 | GM_A167979 | 2764 | 2999 |
| 63010440953 | pMON101819 | GM_A167968 | 3261 | 2464 |
| 63010440814 | pMON101819 | GM_A167984 | 2671 | 2255 |
| 63010440991 | pMON101819 | GM_A167991 | 52 | 55 |
| 63010440686 | pMON101820 | GM_A167466 | 3120 | 3112 |

TABLE 7-continued

*Xenorhabdus bovienii* AK mutant events and wild-type seeds for planting

| Serial Number | Construct | Event | Ser | Thr |
|---|---|---|---|---|
| 63010440636 | pMON101820 | GM_A167452 | 2705 | 2976 |
| 63010440864 | pMON101820 | GM_A167461 | 2844 | 2664 |
| 63010441347 | pMON101820 | GM_A167464 | 28 | 35 |
| 63010441119 | pMON101822 | GM_A166658 | 2419 | 3106 |
| 63010441385 | pMON101822 | GM_A166659 | 2446 | 2751 |
| 63010441272 | pMON101822 | GM_A166646 | 2286 | 2199 |
| 63010440383 | pMON101822 | GM_A166657 | 222 | 89 |
| 60052672132 | control | 1471 | 128 | 31 |
| 60052716946 | control | 1478 | 81 | 30 |
| 60052672029 | control | 1471 | 86 | 28 |
| 60052716960 | control | 1478 | 74 | 27 |
| 60052716958 | control | 1478 | 74 | 27 |
| 60052716972 | control | 1478 | 84 | 27 |

From the examples given, the present invention thus provides isolated feedback-insensitive aspartate kinase genes that are useful for increasing the expression of free threonine and other aspartate-derived amino acids in soybean plants. The present invention also provides a method to produce high free threonine soybean seed via identification of feedback-resistant AK enzymes that can be overexpressed in developing soybean seeds. Additionally, the current invention provides a method to enhance plant nitrogen metabolism and crop growth performance.

Having illustrated and described the principles of the present invention, it should be apparent to persons skilled in the art that the invention can be modified in arrangement and detail without departing from such principles. We claim all modifications that are within the spirit and scope of the appended claims. All patent documents cited in this specification are incorporated herein by reference to the same extent as if each individual was specifically and individually indicated to be incorporated by reference.

The invention claimed is:

1. A polynucleotide comprising a nucleic acid sequence selected from the group consisting of:
   (a) a nucleic acid sequence at least 90% identical to SEQ ID NO: 1 wherein the sequence encodes a polypeptide exhibiting aspartate kinase (AK) activity that is not subject to end-product inhibition by lysine and/or threonine and comprises at least one amino acid substitution at a position corresponding to amino acids 257 or 359 of SEQ ID NO:7; and
   (b) a nucleic acid sequence encoding a polypeptide at least 90% identical to SEQ ID NO: 8 exhibiting aspartate kinase (AK) activity that is not subject to end-product inhibition by lysine and/or threonine and comprises at least one amino acid substitution at a position corresponding to amino acids 257 or 359 of said SEQ ID NO:8,
   wherein said polynucleotide is operably linked to a heterologous promoter functional in a plant cell,
   wherein expression of the nucleic acid sequence in a plant cell increases the level of free threonine about 10 to about 100 times relative to a control plant cell not expressing the nucleic acid.

2. The polynucleotide of claim 1 comprising a nucleic acid sequence with at least 91% to 95% or 96% to 99% identity to SEQ ID NO: 1.

3. The polynucleotide of claim 1, wherein the nucleic acid sequence comprises at least 95% identity to SEQ ID NO: 1.

4. The polynucleotide of claim 1, wherein the nucleic acid sequence comprises SEQ ID NO: 1; SEQ ID NO: 2; or SEQ ID NO: 4.

5. The polynucleotide of claim 1, wherein the nucleic acid sequence encodes a polypeptide at least 95% identical to SEQ ID NO:8.

6. The polynucleotide of claim 1, wherein the amino acid substitution is E257K and/or T359I.

7. The polynucleotide of claim 1, wherein the nucleic acid sequence encodes a polypeptide comprising amino acid substitutions at said positions 257 and 359.

8. The polynucleotide of claim 1, wherein the nucleic acid sequence encodes the polypeptide SEQ ID NO: 7; SEQ ID NO: 8; or SEQ ID NO: 9.

9. A recombinant DNA construct comprising a polynucleotide according to claim 1.

10. The recombinant DNA construct according to claim 9, wherein the promoter is a CaMV 35S promoter, a 7Sα' promoter or a USP99 promoter.

11. The recombinant DNA construct according to claim 9, wherein the promoter is a tissue- and/or organ-specific promoter.

12. The recombinant DNA construct according to claim 9, wherein the promoter is a seed-specific promoter.

13. A transformed cell comprising a polynucleotide according to claim 1.

14. A transgenic plant comprising a polynucleotide according to claim 1.

15. The transgenic plant of claim 14, which is a monocotyledonous plant.

16. The transgenic plant of claim 14, which is a dicotyledonous plant.

17. The transgenic plant of claim 14, wherein the plant is selected from the group consisting of cotton, wheat, sugarcane, sugarbeets, soybean, rice, canola, corn, sorghum, barley, alfalfa, *Brassica* and *Arabidopsis*.

18. A plant part comprising a polynucleotide according to claim 1.

19. A food product comprising a polynucleotide according to claim 1.

20. The food product of claim 19, further defined as a human food product.

21. The food product of claim 19, further defined as animal feed.

22. A seed comprising a polynucleotide according to claim 1.

23. A meal or flour comprising a polynucleotide according to claim 1.

24. A method of transforming a plant cell comprising introducing into the plant cell a polynucleotide according to claim 1.

25. A method of producing a transformed plant comprising:
   a) obtaining a plant cell comprising a polynucleotide according to claim 1; and
   b) regenerating a plant from said cell.

26. A method for increasing the total free amino acid content of a plant comprising: transforming a plant with a plant transformation vector comprising the polynucleotide of claim 1, thereby increasing the free amino acid content of a plant part of the transformed plant compared to an untransformed control plant, wherein the free threonine in the plant part is increased from about 10 to about 100 times relative to a control plant part not comprising the polynucleotide.

27. The polynucleotide of claim 1, wherein expression of the nucleic acid sequence in the plant cell increases the level of free threonine in the plant cell about 50 to about 100 times relative to a control plant cell not expressing the nucleic acid sequence.

28. The polynucleotide of claim 1, wherein expression of the nucleic acid sequence in the plant cell increases the level of free threonine in the plant cell about 67 to about 100 times relative to a control plant cell not expressing the nucleic acid sequence.

29. The plant part of claim 18, wherein the level of free threonine in the plant part is about 67 to about 100 times relative to a control plant part not comprising the polynucleotide.

30. The method of claim 26, wherein the level of free threonine in the plant part is increased about 67 to about 100 times relative to a control plant part not comprising the polynucleotide.

31. The method of claim 26, wherein the plant is a soybean plant.

32. The transgenic plant of claim 14, wherein the plant is a soybean plant.

* * * * *

SEQUENCE LISTING

<160> NUMBER OF SEQ ID NOS: 23

<210> SEQ ID NO 1
<211> LENGTH: 1374
<212> TYPE: DNA
<213> ORGANISM: Xenorhabdus bovienii

<400> SEQUENCE: 1

```
atgtgtgctg tttcatctac ttacccacag tatgttgtcg caaaattcgg cggtaccagt     60
gtggcagact ttgatgccat gaatcactgt gccgatatta ttctggcaaa cgcagatgtc    120
cgcgtagtcg ttttgtccgc ttctgcgggg gtgactaatt tgctggtcgc attggcgacg    180
ggctgtgata acgataaacg taaaaagtgc ctgaaacaga tccgtgacat tcaatatgcg    240
attattgacc gattaaatga cgtgaatgtg atatgtgaag aaattgatcg cctgctggaa    300
aatatcgaga tgttgtcaga agccgcatca ttggcaacct ctgaggcgtt aactgatgaa    360
ttggtcagcc acggtgaagt gatgtccaca ttgctattcg tagaattact gcgtcaacgc    420
aatgtaaatg cagagtggtt tgatatccgc agggtcatgc gaacgaatga tcacttcgga    480
cgagcagaac cagactccct tcaactccat atatcggcgg ttgagctcct tcagcctcgt    540
ttgaataata cagttgttat cacacaaggt tttatcggca gagaagaaaa aggccgcaca    600
actacactgg gacgtggtgg cagtgattat accgccgcct tactcggcga agcgctgaat    660
ttacagcgtg ttgatatttg gacggatgtt cccggcatct ataccactga tccccgtgtt    720
gcaccaacag ccaagcgcat cgataaaatt gcatttgatg aggcagcaaa gatggcgaca    780
tttggtgcta agatcctcca cccagctacg ttgctacctg ccattcgttg cggtattcct    840
gtttttgttg gatcaagtaa agatccacag gccggcggca cactggtttg tgacaaaacc    900
gaaaacccgc ccctgtttcg tgcactggca ttacgccgca aacagacgtt attaaccttg    960
cacagcctaa aaatgttaca tgcaaggggc tttctggcgg aagtttttac gctgctttta   1020
cgccataaca tttcagtaga tttgattacc acctcagaag tcagtgtcgc cctaacgctg   1080
gatacaactg gctctaccag caccaatggc agtctgctga ctaatgctct gctgaccgaa   1140
ctttctacat tatgtcgtgt agaagttgaa gaagatctgg cgctggtggc aattatcggt   1200
aatgagcttt cacaggctaa agggttgggg aaagaaattt ttggcacact ggaatctttt   1260
aatatccgga tgatcagcta tggcgcaagc agccacaatg tatgtttgct cgttcccggt   1320
caagatgcgg aatcagtcat tcagaaactg catcagaatt tgtttaaggt gtga         1374
```

<210> SEQ ID NO 2
<211> LENGTH: 1374
<212> TYPE: DNA
<213> ORGANISM: Xenorhabdus bovienii

<400> SEQUENCE: 2

```
atgtgtgctg tttcatctac ttacccacag tatgttgtcg caaaattcgg cggtaccagt     60
gtggcagact ttgatgccat gaatcactgt gccgatatta ttctggcaaa cgcagatgtc    120
cgcgtagtcg ttttgtccgc ttctgcgggg gtgactaatt tgctggtcgc attggcgacg    180
ggctgtgata acgataaacg taaaaagtgc ctgaaacaga tccgtgacat tcaatatgcg    240
attattgacc gattaaatga cgtgaatgtg atatgtgaag aaattgatcg cctgctggaa    300
aatatcgaga tgttgtcaga agccgcatca ttggcaacct ctgaggcgtt aactgatgaa    360
ttggtcagcc acggtgaagt gatgtccaca ttgctattcg tagaattact gcgtcaacgc    420
aatgtaaatg cagagtggtt tgatatccgc agggtcatgc gaacgaatga tcacttcgga    480
```

-continued

```
cgagcagaac cagactccct tcaactccat atatcggcgg ttgagctcct tcagcctcgt      540
ttgaataata cagttgttat cacacaaggt tttatcggca gagaagaaaa aggccgcaca      600
actacactgg gacgtggtgg cagtgattat accgccgcct tactcggcga agcgctgaat      660
ttacagcgtg ttgatatttg gacgatgtt cccggcatct ataccactga tccccgtgtt      720
gcaccaacag ccaagcgcat cgataaaatt gcatttgatg aggcagcaga gatggcgaca      780
tttggtgcta agatcctcca cccagctacg ttgctacctg ccattcgttg cggtattcct      840 gttttttgttg gatcaagtaa agatccacag gccggcggca cactggtttg tgacaaaacc      900
gaaaaaccgc ccctgtttcg tgcactggca ttacgccgca acagacgtt attaaccttg      960 cacagcctaa aaatgttaca tgcaaggggc tttctggcgg aagttttttac gctgcttttta     1020 cgccataaca tttcagtaga tttgattacc acctcagaag tcagtgtcgc cctaatcctg     1080
gatacaactg gctctaccag caccaatggc agtctgctga ctaatgctct gctgaccgaa     1140
ctttctacat tatgtcgtgt agaagttgaa gaagatctgg cgctggtggc aattatcggt     1200
aatgagcttt cacaggctaa agggttgggg aaagaaattt ttggcacact ggaatctttt     1260
aatatccgga tgatcagcta tggcgcaagc agccacaatg tatgtttgct cgttcccggt     1320
caagatgcgg aatcagtcat tcagaaactg catcagaatt tgtttaaggt gtga            1374
```

<210> SEQ ID NO 3
<211> LENGTH: 1374
<212> TYPE: DNA
<213> ORGANISM: Xenorhabdus bovienii

<400> SEQUENCE: 3

```
atgtgcgctg tttcttcaac ttaccctcaa tacgttgtgg ctaagttcgg tggaacttct       60
gttgctgatt tcgatgctat gaaccactgc gctgatatta tcttggctaa cgctgatgtt      120
agagttgtgg ttttgtctgc ttctgctggt gttactaact tgcttgttgc tttggctact      180
ggttgcgata acgataagag aaagaaatgc ttgaagcaaa ttagagatat tcaatacgct      240
attatcgata gattgaacga tgttaacgtt atttgcgagg aaattgatag attgcttgag      300
aacattgaga tgttgtctga ggctgcatct ttggctactt ctgaggcttt gactgatgag      360
ttggtttcac acggtgaggt tatgtcaact ttgcttttcg ttgagttgct tagacaaaga      420
aacgttaacg ctgagtggtt cgatattagg cgtgttatga ggactaacga tcacttcggt      480
agggctgagc ctgattcatt gcaattgcac atttcagctg ttgagcttct ccaacctagg      540
cttaacaata ctgtggtcat tactcaaggt ttcattggta gggaggaaaa gggtaggact      600
accactcttg aagggggagg ctcagattat actgcagccc ttctcggaga ggcacttaat      660
cttcagcgtg tggatatttg gaccgacgtg cctggaattt ataccacaga cccacgtgtg      720
gcaccaaccg caaagcgtat tgacaagatc gcattcgacg aggcagccga gatggcaacc      780
ttcggagcaa agatccttca cccagcaacc cttctcccag caatccgctg tggaatccca      840
gtgtttgtgg gatccagtaa ggaccccag gccggaggca ccttgtgtg tgacaagacc      900 gaaaatcccc cgcttttttcg cgcccttgcc cttcgccgaa agcagaccct cctgaccctc      960
cattccctca aaatgctcca tgcccgcggc tttctcgccg aagtgtttac cctcctgctc     1020
cgacataata tctccgtgga cctcatcaca cgtccgaag tctccgtcgc cctcatcctg     1080
gacacaacgg gcagtacaag tacaaatggc agtctgctaa caaatgccct gctaacagaa     1140
ctgagtacac tgtgtcgggt cgaagtcgaa gaagacctgg ccctagtcgc catcataggc     1200
```

| aatgaactaa gccaggcgaa agggctaggg aaagaaatat ttgggacatt agaaagcttt | 1260 |
| aatatacgga tgataagcta tggggcgagc tcgcataatg tctgtttatt agtacccggg | 1320 |
| caggacgcgg aatcggtaat acagaaatta catcagaatt tatttaaagt atga | 1374 |

<210> SEQ ID NO 4
<211> LENGTH: 1374
<212> TYPE: DNA
<213> ORGANISM: Xenorhabdus bovienii

<400> SEQUENCE: 4

| atgtgtgctg tttcatctac ttacccacag tatgttgtcg caaaattcgg cggtaccagt | 60 |
| gtggcagact tgatgccat gaatcactgt gccgatatta ttctggcaaa cgcagatgtc | 120 |
| cgcgtagtcg ttttgtccgc ttctgcgggg gtgactaatt tgctggtcgc attggcgacg | 180 |
| ggctgtgata acgataaacg taaaaagtgc ctgaaacaga tccgtgacat tcaatatgcg | 240 |
| attattgacc gattaaatga cgtgaatgtg atatgtgaag aaattgatcg cctgctggaa | 300 |
| aatatcgaga tgttgtcaga agccgcatca ttggcaacct ctgaggcgtt aactgatgaa | 360 |
| ttggtcagcc acggtgaagt gatgtccaca ttgctattcg tagaattact gcgtcaacgc | 420 |
| aatgtaaatg cagagtggtt tgatatccgc agggtcatgc gaacgaatga tcacttcgga | 480 |
| cgagcagaac cagactccct tcaactccat atatcggcgg ttgagctcct tcagcctcgt | 540 |
| ttgaataata cagttgttat cacacaaggt tttatcggca gagaagaaaa aggccgcaca | 600 |
| actacactgg gacgtggtgg cagtgattat accgccgcct tactcggcga agcgctgaat | 660 |
| ttacagcgtg ttgatatttg gacggatgtt cccggcatct ataccactga tccccgtgtt | 720 |
| gcaccaacag ccaagcgcat cgataaaatt gcatttgatg aggcagcaaa gatggcgaca | 780 |
| tttggtgcta gatcctcca cccagctacg ttgctacctg ccattcgttg cggtattcct | 840 |
| gtttttgttg gatcaagtaa agatccacag gccggcggca cactggtttg tgacaaaacc | 900 |
| gaaaacccgc ccctgtttcg tgcactggca ttacgccgca acagacgttt attaaccttg | 960 |
| cacagcctaa aaatgttaca tgcaaggggc tttctggcgg aagttttttac gctgcttttta | 1020 |
| cgccataaca tttcagtaga tttgattacc acctcagaag tcagtgtcgc cctaatcctg | 1080 |
| gatacaactg gctctaccag caccaatggc agtctgctga ctaatgctct gctgaccgaa | 1140 |
| ctttctacat tatgtcgtgt agaagttgaa gaagatctgg cgctggtggc aattatcggt | 1200 |
| aatgagcttt cacaggctaa agggttgggg aaagaaattt ttggcacact ggaatctttt | 1260 |
| aatatccgga tgatcagcta tggcgcaagc agccacaatg tatgtttgct cgttcccggt | 1320 |
| caagatgcgg aatcagtcat tcagaaactg catcagaatt tgtttaaggt gtga | 1374 |

<210> SEQ ID NO 5
<211> LENGTH: 1320
<212> TYPE: DNA
<213> ORGANISM: Xenorhabdus bovienii

<400> SEQUENCE: 5

| atgtgtgctg tttcatctac ttacccacag tatgttgtcg caaaattcgg cggtaccagt | 60 |
| gtggcagact tgatgccat gaatcactgt gccgatatta tt

```
ttggtcagcc acggtgaagt gatgtccaca ttgctattcg tagaattact gcgtcaacgc    420
aatgtaaatg cagagtggtt tgatatccgc agggtcatgc gaacgaatga tcacttcgga    480
cgagcagaac cagactccct tcaactccat atatcggcgg ttgagctcct tcagcctcgt    540
ttgaataata cagttgttat cacacaaggt tttatcggca gagaagaaaa aggccgcaca    600
actacactgg gacgtggtgg cagtgattat accgccgcct tactcggcga agcgctgaat    660
ttacagcgtg ttgatatttg gacggatgtt cccggcatct ataccactga tccccgtgtt    720
gcaccaacag ccaagcgcat cgataaaatt gcatttgatg aggcagcaga gatggcgaca    780
tttggtgcta agatcctcca cccagctacg ttgctacctg ccattcgttg cggtattcct    840 gttttgttg gatcaagtaa agatccacag gccggcggca cactggtttg tgacaaaacc    900
gaaaacccgc ccctgtttcg tgcactggca ttacgccgca acagacgtt attaaccttg    960 cacagcctaa aaatgttaca tgcaaggggc tttctggcgg aagttttac gctgctttta    1020 cgccataaca ttgaattctc taccagcacc aatggcagtc tgctgactaa tgctctgctg    1080
accgaacttt ctacattatg tcgtgtagaa gttgaagaag atctggcgct ggtggcaatt    1140
atcggtaatg agctttcaca ggctaaaggg ttggggaaag aaattttggg cacactggaa    1200
tcttttaata tccggatgat cagctatggc gcaagcagcc acaatgtatg tttgctcgtt    1260
cccggtcaag atgcggaatc agtcattcag aaactgcatc agaatttgtt taaggtgtga    1320
```

<210> SEQ ID NO 6
<211> LENGTH: 1374
<212> TYPE: DNA
<213> ORGANISM: Xenorhabdus bovienii

<400> SEQUENCE: 6

```
atgtgtgctg tttcatctac ttacccacag tatgttgtcg caaaattcgg cggtaccagt    60
gtggcagact ttgatgccat gaatcactgt gccgatatta ttctggcaaa cgcagatgtc    120
cgcgtagtcg ttttgtccgc ttctgcgggg gtgactaatt tgctggtcgc attggcgacg    180
ggctgtgata acgataaacg taaaaagtgc ctgaaacaga tccgtgacat tcaatatgcg    240
attattgacc gattaaatga cgtgaatgtg atatgtgaag aaattgatcg cctgctggaa    300
aatatcgaga tgttgtcaga agccgcatca ttggcaacct ctgaggcgtt aactgatgaa    360
ttggtcagcc acggtgaagt gatgtccaca ttgctattcg tagaattact gcgtcaacgc    420
aatgtaaatg cagagtggtt tgatatccgc agggtcatgc gaacgaatga tcacttcgga    480
cgagcagaac cagactccct tcaactccat atatcggcgg ttgagctcct tcagcctcgt    540
ttgaataata cagttgttat cacacaaggt tttatcggca gagaagaaaa aggccgcaca    600
actacactgg gacgtggtgg cagtgattat accgccgcct tactcggcga agcgctgaat    660
ttacagcgtg ttgatatttg gacggatgtt cccggcatct ataccactga tccccgtgtt    720
gcaccaacag ccaagcgcat cgataaaatt gcatttgatg aggcagcaga gatggcgaca    780
tttggtgcta agatcctcca cccagctacg ttgctacctg ccattcgttg cggtattcct    840 gttttgttg gatcaagtaa agatccacag gccggcggca cactggtttg tgacaaaacc    900
gaaaacccgc ccctgtttcg tgcactggca ttacgccgca acagacgtt attaaccttg    960 cacagcctaa aaatgttaca tgcaaggggc tttctggcgg aagttttac gctgctttta    1020 cgccataaca tttcagtaga tttgattacc acctcagaag tcagtgtcgc cctaacgctg    1080
gatacaactg gctctaccag caccaatggc agtctgctga ctaatgctct gctgaccgaa    1140
```

```
cttttctacat tatgtcgtgt agaagttgaa gaagatctgg cgctggtggc aattatcggt    1200
aatgagcttt cacaggctaa agggttgggg aaagaaattt ttggcacact ggaatctttt    1260
aatatccgga tgatcagcta tggcgcaagc agccacaatg tatgtttgct cgttcccggt    1320
caagatgcgg aatcagtcat tcagaaactg catcagaatt tgtttaaggt gtga          1374
```

```
<210> SEQ ID NO 7
<211> LENGTH: 457
<212> TYPE: PRT
<213> ORGANISM: Xenorhabdus bovienii

<400> SEQUENCE: 7

Met Cys Ala Val Ser Ser Thr Tyr Pro Gln Tyr Val Val Ala Lys Phe
1               5                   10                  15

Gly Gly Thr Ser Val Ala Asp Phe Asp Ala Met Asn His Cys Ala Asp
            20                  25                  30

Ile Ile Leu Ala Asn Ala Asp Val Arg Val Val Leu Ser Ala Ser
        35                  40                  45

Ala Gly Val Thr Asn Leu Leu Val Ala Leu Ala Thr Gly Cys Asp Asn
    50                  55                  60

Asp Lys Arg Lys Lys Cys Leu Lys Gln Ile Arg Asp Ile Gln Tyr Ala
65                  70                  75                  80

Ile Ile Asp Arg Leu Asn Asp Val Asn Val Ile Cys Glu Glu Ile Asp
                85                  90                  95

Arg Leu Leu Glu Asn Ile Glu Met Leu Ser Glu Ala Ala Ser Leu Ala
            100                 105                 110

Thr Ser Glu Ala Leu Thr Asp Glu Leu Val Ser His Gly Glu Val Met
        115                 120                 125

Ser Thr Leu Leu Phe Val Glu Leu Leu Arg Gln Arg Asn Val Asn Ala
    130                 135                 140

Glu Trp Phe Asp Ile Arg Arg Val Met Arg Thr Asn Asp His Phe Gly
145                 150                 155                 160

Arg Ala Glu Pro Asp Ser Leu Gln Leu His Ile Ser Ala Val Glu Leu
                165                 170                 175

Leu Gln Pro Arg Leu Asn Asn Thr Val Val Ile Thr Gln Gly Phe Ile
            180                 185                 190

Gly Arg Glu Glu Lys Gly Arg Thr Thr Thr Leu Gly Arg Gly Gly Ser
        195                 200                 205

Asp Tyr Thr Ala Ala Leu Leu Gly Glu Ala Leu Asn Leu Gln Arg Val
    210                 215                 220

Asp Ile Trp Thr Asp Val Pro Gly Ile Tyr Thr Thr Asp Pro Arg Val
225                 230                 235                 240

Ala Pro Thr Ala Lys Arg Ile Asp Lys Ile Ala Phe Asp Glu Ala
                245                 250                 255

Lys Met Ala Thr Phe Gly Ala Lys Ile Leu His Pro Ala Thr Leu Leu
            260                 265                 270

Pro Ala Ile Arg Cys Gly Ile Pro Val Phe Val Gly Ser Ser Lys Asp
        275                 280                 285

Pro Gln Ala Gly Gly Thr Leu Val Cys Asp Lys Thr Glu Asn Pro Pro
    290                 295                 300

Leu Phe Arg Ala Leu Ala Leu Arg Arg Lys Gln Thr Leu Leu Thr Leu
305                 310                 315                 320

His Ser Leu Lys Met Leu His Ala Arg Gly Phe Leu Ala Glu Val Phe
                325                 330                 335
```

```
Thr Leu Leu Leu Arg His Asn Ile Ser Val Asp Leu Ile Thr Thr Ser
            340                 345                 350

Glu Val Ser Val Ala Leu Thr Leu Asp Thr Thr Gly Ser Thr Ser Thr
        355                 360                 365

Asn Gly Ser Leu Leu Thr Asn Ala Leu Leu Thr Glu Leu Ser Thr Leu
    370                 375                 380

Cys Arg Val Glu Val Glu Glu Asp Leu Ala Leu Val Ala Ile Ile Gly
385                 390                 395                 400

Asn Glu Leu Ser Gln Ala Lys Gly Leu Gly Lys Glu Ile Phe Gly Thr
                405                 410                 415

Leu Glu Ser Phe Asn Ile Arg Met Ile Ser Tyr Gly Ala Ser Ser His
            420                 425                 430

Asn Val Cys Leu Leu Val Pro Gly Gln Asp Ala Glu Ser Val Ile Gln
            435                 440                 445

Lys Leu His Gln Asn Leu Phe Lys Val
        450                 455

<210> SEQ ID NO 8
<211> LENGTH: 457
<212> TYPE: PRT
<213> ORGANISM: Xenorhabdus bovienii

<400> SEQUENCE: 8

Met Cys Ala Val Ser Ser Thr Tyr Pro Gln Tyr Val Val Ala Lys Phe
1               5                   10                  15

Gly Gly Thr Ser Val Ala Asp Phe Asp Ala Met Asn His Cys Ala Asp
            20                  25                  30

Ile Ile Leu Ala Asn Ala Asp Val Arg Val Val Leu Ser Ala Ser
            35                  40                  45

Ala Gly Val Thr Asn Leu Leu Val Ala Leu Ala Thr Gly Cys Asp Asn
    50                  55                  60

Asp Lys Arg Lys Lys Cys Leu Lys Gln Ile Arg Asp Ile Gln Tyr Ala
65                  70                  75                  80

Ile Ile Asp Arg Leu Asn Asp Val Asn Val Ile Cys Glu Glu Ile Asp
                85                  90                  95

Arg Leu Leu Glu Asn Ile Glu Met Leu Ser Glu Ala Ala Ser Leu Ala
            100                 105                 110

Thr Ser Glu Ala Leu Thr Asp Glu Leu Val Ser His Gly Glu Val Met
        115                 120                 125

Ser Thr Leu Leu Phe Val Glu Leu Leu Arg Gln Arg Asn Val Asn Ala
    130                 135                 140

Glu Trp Phe Asp Ile Arg Arg Val Met Arg Thr Asn Asp His Phe Gly
145                 150                 155                 160

Arg Ala Glu Pro Asp Ser Leu Gln Leu His Ile Ser Ala Val Glu Leu
                165                 170                 175

Leu Gln Pro Arg Leu Asn Asn Thr Val Val Ile Thr Gln Gly Phe Ile
            180                 185                 190

Gly Arg Glu Glu Lys Gly Arg Thr Thr Thr Leu Gly Arg Gly Gly Ser
        195                 200                 205

Asp Tyr Thr Ala Ala Leu Leu Gly Glu Ala Leu Asn Leu Gln Arg Val
    210                 215                 220

Asp Ile Trp Thr Asp Val Pro Gly Ile Tyr Thr Thr Asp Pro Arg Val
225                 230                 235                 240

Ala Pro Thr Ala Lys Arg Ile Asp Lys Ile Ala Phe Asp Glu Ala Ala
                245                 250                 255
```

```
Glu Met Ala Thr Phe Gly Ala Lys Ile Leu His Pro Ala Thr Leu Leu
            260                 265                 270

Pro Ala Ile Arg Cys Gly Ile Pro Val Phe Val Gly Ser Ser Lys Asp
        275                 280                 285

Pro Gln Ala Gly Gly Thr Leu Val Cys Asp Lys Thr Glu Asn Pro Pro
    290                 295                 300

Leu Phe Arg Ala Leu Ala Leu Arg Arg Lys Gln Thr Leu Leu Thr Leu
305                 310                 315                 320

His Ser Leu Lys Met Leu His Ala Arg Gly Phe Leu Ala Glu Val Phe
                325                 330                 335

Thr Leu Leu Arg His Asn Ile Ser Val Asp Leu Ile Thr Thr Ser
            340                 345                 350

Glu Val Ser Val Ala Leu Ile Leu Asp Thr Thr Gly Ser Thr Ser Thr
        355                 360                 365

Asn Gly Ser Leu Leu Thr Asn Ala Leu Leu Thr Glu Leu Ser Thr Leu
    370                 375                 380

Cys Arg Val Glu Val Glu Glu Asp Leu Ala Leu Val Ala Ile Ile Gly
385                 390                 395                 400

Asn Glu Leu Ser Gln Ala Lys Gly Leu Gly Lys Glu Ile Phe Gly Thr
                405                 410                 415

Leu Glu Ser Phe Asn Ile Arg Met Ile Ser Tyr Gly Ala Ser Ser His
            420                 425                 430

Asn Val Cys Leu Leu Val Pro Gly Gln Asp Ala Glu Ser Val Ile Gln
        435                 440                 445

Lys Leu His Gln Asn Leu Phe Lys Val
    450                 455

<210> SEQ ID NO 9
<211> LENGTH: 457
<212> TYPE: PRT
<213> ORGANISM: Xenorhabdus bovienii

<400> SEQUENCE: 9

Met Cys Ala Val Ser Ser Thr Tyr Pro Gln Tyr Val Val Ala Lys Phe
1               5                   10                  15

Gly Gly Thr Ser Val Ala Asp Phe Asp Ala Met Asn His Cys Ala Asp
            20                  25                  30

Ile Ile Leu Ala Asn Ala Asp Val Arg Val Val Leu Ser Ala Ser
        35                  40                  45

Ala Gly Val Thr Asn Leu Leu Val Ala Leu Ala Thr Gly Cys Asp Asn
    50                  55                  60

Asp Lys Arg Lys Lys Cys Leu Lys Gln Ile Arg Asp Ile Gln Tyr Ala
65                  70                  75                  80

Ile Ile Asp Arg Leu Asn Asp Val Asn Val Ile Cys Glu Glu Ile Asp
                85                  90                  95

Arg Leu Leu Glu Asn Ile Glu Met Leu Ser Glu Ala Ala Ser Leu Ala
            100                 105                 110

Thr Ser Glu Ala Leu Thr Asp Glu Leu Val Ser His Gly Glu Val Met
        115                 120                 125

Ser Thr Leu Leu Phe Val Glu Leu Leu Arg Gln Arg Asn Val Asn Ala
    130                 135                 140

Glu Trp Phe Asp Ile Arg Arg Val Met Arg Thr Asn Asp His Phe Gly
145                 150                 155                 160

Arg Ala Glu Pro Asp Ser Leu Gln Leu His Ile Ser Ala Val Glu Leu
```

```
                165                 170                 175
Leu Gln Pro Arg Leu Asn Asn Thr Val Val Ile Thr Gln Gly Phe Ile
            180                 185                 190

Gly Arg Glu Glu Lys Gly Arg Thr Thr Leu Gly Arg Gly Gly Ser
        195                 200                 205

Asp Tyr Thr Ala Ala Leu Leu Gly Glu Ala Leu Asn Leu Gln Arg Val
        210                 215                 220

Asp Ile Trp Thr Asp Val Pro Gly Ile Tyr Thr Thr Asp Pro Arg Val
225                 230                 235                 240

Ala Pro Thr Ala Lys Arg Ile Asp Lys Ile Ala Phe Asp Glu Ala Ala
                245                 250                 255

Lys Met Ala Thr Phe Gly Ala Lys Ile Leu His Pro Ala Thr Leu Leu
                260                 265                 270

Pro Ala Ile Arg Cys Gly Ile Pro Val Phe Val Gly Ser Ser Lys Asp
            275                 280                 285

Pro Gln Ala Gly Gly Thr Leu Val Cys Asp Lys Thr Glu Asn Pro Pro
        290                 295                 300

Leu Phe Arg Ala Leu Ala Leu Arg Arg Lys Gln Thr Leu Leu Thr Leu
305                 310                 315                 320

His Ser Leu Lys Met Leu His Ala Arg Gly Phe Leu Ala Glu Val Phe
                325                 330                 335

Thr Leu Leu Leu Arg His Asn Ile Ser Val Asp Leu Ile Thr Thr Ser
                340                 345                 350

Glu Val Ser Val Ala Leu Ile Leu Asp Thr Thr Gly Ser Thr Ser Thr
            355                 360                 365

Asn Gly Ser Leu Leu Thr Asn Ala Leu Leu Thr Glu Leu Ser Thr Leu
    370                 375                 380

Cys Arg Val Glu Val Glu Glu Asp Leu Ala Leu Val Ala Ile Ile Gly
385                 390                 395                 400

Asn Glu Leu Ser Gln Ala Lys Gly Leu Gly Lys Glu Ile Phe Gly Thr
                405                 410                 415

Leu Glu Ser Phe Asn Ile Arg Met Ile Ser Tyr Gly Ala Ser Ser His
                420                 425                 430

Asn Val Cys Leu Leu Val Pro Gly Gln Asp Ala Glu Ser Val Ile Gln
            435                 440                 445

Lys Leu His Gln Asn Leu Phe Lys Val
        450                 455

<210> SEQ ID NO 10
<211> LENGTH: 439
<212> TYPE: PRT
<213> ORGANISM: Xenorhabdus bovienii

<400> SEQUENCE: 10

Met Cys Ala Val Ser Ser Thr Tyr Pro Gln Tyr Val Val Ala Lys Phe
1               5                   10                  15

Gly Gly Thr Ser Val Ala Asp Phe Asp Ala Met Asn His Cys Ala Asp
            20                  25                  30

Ile Ile Leu Ala Asn Ala Asp Val Arg Val Val Leu Ser Ala Ser
        35                  40                  45

Ala Gly Val Thr Asn Leu Leu Val Ala Leu Ala Thr Gly Cys Asp Asn
    50                  55                  60

Asp Lys Arg Lys Lys Cys Leu Lys Gln Ile Arg Asp Ile Gln Tyr Ala
65                  70                  75                  80
```

-continued

```
Ile Ile Asp Arg Leu Asn Asp Val Asn Val Ile Cys Glu Glu Ile Asp
            85                  90                  95

Arg Leu Leu Glu Asn Ile Glu Met Leu Ser Glu Ala Ala Ser Leu Ala
        100                 105                 110

Thr Ser Glu Ala Leu Thr Asp Glu Leu Val Ser His Gly Glu Val Met
    115                 120                 125

Ser Thr Leu Leu Phe Val Glu Leu Leu Arg Gln Arg Asn Val Asn Ala
130                 135                 140

Glu Trp Phe Asp Ile Arg Arg Val Met Arg Thr Asn Asp His Phe Gly
145                 150                 155                 160

Arg Ala Glu Pro Asp Ser Leu Gln Leu His Ile Ser Ala Val Glu Leu
                165                 170                 175

Leu Gln Pro Arg Leu Asn Asn Thr Val Val Ile Thr Gln Gly Phe Ile
            180                 185                 190

Gly Arg Glu Glu Lys Gly Arg Thr Thr Thr Leu Gly Arg Gly Gly Ser
        195                 200                 205

Asp Tyr Thr Ala Ala Leu Leu Gly Glu Ala Leu Asn Leu Gln Arg Val
    210                 215                 220

Asp Ile Trp Thr Asp Val Pro Gly Ile Tyr Thr Thr Asp Pro Arg Val
225                 230                 235                 240

Ala Pro Thr Ala Lys Arg Ile Asp Lys Ile Ala Phe Asp Glu Ala Ala
                245                 250                 255

Glu Met Ala Thr Phe Gly Ala Lys Ile Leu His Pro Ala Thr Leu Leu
            260                 265                 270

Pro Ala Ile Arg Cys Gly Ile Pro Val Phe Val Gly Ser Ser Lys Asp
        275                 280                 285

Pro Gln Ala Gly Gly Thr Leu Val Cys Asp Lys Thr Glu Asn Pro Pro
290                 295                 300

Leu Phe Arg Ala Leu Ala Leu Arg Arg Lys Gln Thr Leu Leu Thr Leu
305                 310                 315                 320

His Ser Leu Lys Met Leu His Ala Arg Gly Phe Leu Ala Glu Val Phe
                325                 330                 335

Thr Leu Leu Leu Arg His Asn Ile Glu Phe Ser Thr Ser Thr Asn Gly
            340                 345                 350

Ser Leu Leu Thr Asn Ala Leu Leu Thr Glu Leu Ser Thr Leu Cys Arg
        355                 360                 365

Val Glu Val Glu Glu Asp Leu Ala Leu Val Ala Ile Ile Gly Asn Glu
    370                 375                 380

Leu Ser Gln Ala Lys Gly Leu Gly Lys Glu Ile Phe Gly Thr Leu Glu
385                 390                 395                 400

Ser Phe Asn Ile Arg Met Ile Ser Tyr Gly Ala Ser Ser His Asn Val
                405                 410                 415

Cys Leu Leu Val Pro Gly Gln Asp Ala Glu Ser Val Ile Gln Lys Leu
            420                 425                 430

His Gln Asn Leu Phe Lys Val
        435
```

<210> SEQ ID NO 11
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 11

```
gggaattcca tatgtgtgct gtttcatc                                          28
```

```
<210> SEQ ID NO 12
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 12
ccgctcgagc accttaaaca aattctgatg                                        30
```

```
<210> SEQ ID NO 13
<211> LENGTH: 264
<212> TYPE: DNA
<213> ORGANISM: Arabidopsis thaliana

<400> SEQUENCE: 13
atggcttcct ctatgctctc ttccgctact atggttgcct ctccggctca ggccactatg       60
gtcgctcctt tcaacggact taagtcctcc gctgccttcc cagccacccg caaggctaac      120
aacgacatta cttccatcac aagcaacggc ggaagagtta actgcatgca ggtgtggcct      180
ccgattggaa agaagaagtt tgagactctc tcttaccttc ctgaccttac cgattccggt      240
ggtcgcgtca actgcatgca ggcc                                             264
```

```
<210> SEQ ID NO 14
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 14
catgccatgg aggccatgtc tgaaattgtt gtc                                    33
```

```
<210> SEQ ID NO 15
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 15
ccggtcgagc tcaaacaaat tactatgcag                                        30
```

```
<210> SEQ ID NO 16
<211> LENGTH: 1347
<212> TYPE: DNA
<213> ORGANISM: Escherichia coli

<400> SEQUENCE: 16
tgtctgaaat tgttgtctcc aaatttggcg gtaccagcgt agctgatttt gacgccatga       60
accgcagcgc tgatattgtg ctttctgatg ccaacgtgcg tttagttgtc ctctcggctt      120
ctgctggtat cactaatctg ctggtcgctt agctgaagg actggaacct ggcgagcgat      180
tcgaaaaact cgacgctatc cgcaacatcc agtttgccat tctggaacgt ctgcgttacc      240
cgaacgttat ccgtgaagag attgaacgtc tgctggagaa cattactgtt ctggcagaag      300
cggcggcgct ggcaacgtct ccggcgctga cagatgagct ggtcagccac ggcgagctga      360
tgtcgaccct gctgtttgtt gagatcctgc gcgaacgcga tgttcaggca cagtggtttg      420
atgtacgtaa agtgatgcgt accaacgacc gatttggtcg tgcagagcca gatatagccg      480
```

```
cgctggcgga actggccgcg ctgcagctgc tcccacgtct caatgaaggc ttagtgatca      540
cccagggatt tatcggtagc gaaaataaag gtcgtacaac gacgcttggc cgtggaggca      600
gcgattatac ggcagccttg ctggcggagg ctttacacgc atctcgtgtt gatatctgga      660
ccgacgtccc gggcatctac accaccgatc cacgcgtagt ttccgcagca aaacgcattg      720
atgaaatcgc gtttgccgaa gcggcagaga tggcaacttt tggtgcaaaa gtactgcatc      780
cggcaacgtt gctacccgca gtacgcagcg atatcccggt ctttgtcggc tccagcaaag      840
acccacgcgc aggtggtacg ctggtgtgca ataaaactga aaatccgccg ctgttccgcg      900
ctctggcgct tcgtcgcaat cagactctgc tcactttgca cagcctgaat atgctgcatt      960
ctcgcggttt cctcgcggaa gttttcggca tcctcgcgcg gcataatatt tcggtagact     1020
taatcaccac gtcagaagtg agcgtggcat aatccttga taccaccggt tcaacctcca     1080
ctggcgatac gttgctgacg caatctctgc tgatggagct ttccgcactg tgtcgggtgg     1140
aggtggaaga aggtctggcg ctggtcgcgt tgattggcaa tgacctgtca aaagcctgcg     1200
gcgttggcaa agaggtattc ggcgtactgg aaccgttcaa cattcgcatg atttgttatg     1260
gcgcatccag ccataacctg tgcttcctgg tgcccggcga agatgccgag caggtggtgc     1320
aaaaactgca tagtaatttg tttgagc                                         1347
```

<210> SEQ ID NO 17
<211> LENGTH: 449
<212> TYPE: PRT
<213> ORGANISM: Escherichia coli

<400> SEQUENCE: 17

```
Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
        50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Val Ala
145                 150                 155                 160

Ala Leu Ala Glu Leu Ala Ala Leu Gln Leu Leu Pro Arg Leu Asn Asp
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
```

```
            210                 215                 220
Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
            340                 345                 350

Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Phe Asn Leu Phe
        435                 440                 445

Glu

<210> SEQ ID NO 18
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 18
ccgctcgagc accttaaaca aattctgatg                                    30

<210> SEQ ID NO 19
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 19
gggaattcca tatgtgtgct gtttcatc                                      28

<210> SEQ ID NO 20
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 20
```

```
gatgaggcag caaagatggc gacatttggt                                              30

<210> SEQ ID NO 21
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 21
accaaatgtc gccatctttg ctgcctcatc                                              30

<210> SEQ ID NO 22
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 22
tcagtgtcgc cctaatcctg gatacaactg                                              30

<210> SEQ ID NO 23
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 23
cagttgtatc caggattagg gcgacactga                                              30
```